United States Patent
Corgie et al.

(10) Patent No.: US 10,993,436 B2
(45) Date of Patent: *May 4, 2021

(54) MAGNETICALLY IMMOBILIZED BIOCIDAL ENZYMES AND BIOCIDAL CHEMICALS

(71) Applicant: ZYMtronix Catalytic Systems, Inc., Ithaca, NY (US)

(72) Inventors: Stephane Cedric Corgie, Ithaca, NY (US); Zachariah Robert Hansen, Ithaca, NY (US)

(73) Assignee: ZYMtronix Catalytic Systems, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/274,135

(22) Filed: Feb. 12, 2019

(65) Prior Publication Data

US 2019/0174745 A1   Jun. 13, 2019

Related U.S. Application Data

(63) Continuation of application No. PCT/US2017/045655, filed on Aug. 6, 2017.

(60) Provisional application No. 62/374,836, filed on Aug. 13, 2016, provisional application No. 62/511,331, filed on May 25, 2017.

(51) Int. Cl.
| | |
|---|---|
| *A01N 25/08* | (2006.01) |
| *A01N 43/90* | (2006.01) |
| *A01N 47/44* | (2006.01) |
| *A01N 59/20* | (2006.01) |
| *A61L 15/18* | (2006.01) |
| *A61L 15/20* | (2006.01) |
| *A61L 15/38* | (2006.01) |
| *A01N 63/10* | (2020.01) |
| *A01N 37/34* | (2006.01) |
| *A01N 47/26* | (2006.01) |
| *A61L 15/42* | (2006.01) |
| *A61L 15/44* | (2006.01) |
| *A61L 15/46* | (2006.01) |

(52) U.S. Cl.
CPC .............. *A01N 25/08* (2013.01); *A01N 37/34* (2013.01); *A01N 43/90* (2013.01); *A01N 47/26* (2013.01); *A01N 47/44* (2013.01); *A01N 59/20* (2013.01); *A01N 63/10* (2020.01); *A61L 15/18* (2013.01); *A61L 15/20* (2013.01); *A61L 15/38* (2013.01); *A61L 15/42* (2013.01); *A61L 15/44* (2013.01); *A61L 15/46* (2013.01); *A61L 2300/11* (2013.01); *A61L 2300/404* (2013.01); *A61L 2300/406* (2013.01); *A61L 2300/602* (2013.01)

(58) Field of Classification Search
CPC ........ A01N 25/08; A01N 43/90; A01N 47/44; A01N 59/20; A61L 15/18; A61L 15/20; A61L 15/38; A61L 15/42; A61L 15/44; A61L 15/46; A61L 2300/11; A61L 2300/404; A61L 2300/406

See application file for complete search history.

(56) References Cited

U.S. PATENT DOCUMENTS

| | | | |
|---|---|---|---|
| 4,152,210 | A | 5/1979 | Robinson et al. |
| 5,460,830 | A | 10/1995 | Kossovsky et al. |
| 5,965,418 | A | 10/1999 | Fuglsang et al. |
| 6,440,711 | B1 | 8/2002 | Dave et al. |
| 6,447,811 | B1 | 9/2002 | Ravensberg et al. |
| 7,241,883 | B2 | 7/2007 | Lugade et al. |
| 7,385,053 | B2 | 6/2008 | Lugade et al. |
| 7,459,145 | B2 | 12/2008 | Bao et al. |
| 7,485,367 | B2 | 2/2009 | Chen et al. |
| 7,731,954 | B2 | 6/2010 | Davis et al. |
| 8,075,793 | B2 | 12/2011 | Moreira et al. |
| 8,188,269 | B1 | 5/2012 | Lugade et al. |
| 8,841,105 | B2 | 9/2014 | Sakai et al. |
| 8,940,179 | B2 | 1/2015 | Suh et al. |
| 9,035,003 | B2 | 5/2015 | Hanson et al. |
| 9,597,672 | B2 | 3/2017 | Corgie et al. |
| 9,765,324 | B2 | 9/2017 | Corgie et al. |

(Continued)

FOREIGN PATENT DOCUMENTS

| | | |
|---|---|---|
| CN | 1580233 A | 2/2005 |
| CN | 101109016 A | 1/2008 |

(Continued)

OTHER PUBLICATIONS

Merriam-Webster, "matrix," <https://www.merriam-webster.com/dictionary/matrix>, Copyright 2020 Merriam-Webster, Incorporated, p. 2.*
"Agriculture," Merriam-Webster, <https://www.merriam-webster.com/dictionary/agriculture>, published Jun. 5, 2012, p. 1.*
Supplementary European Search Report dated Sep. 29, 2016 issued in EP 13 84 4083.9.
Supplementary Partial European Search Report dated Apr. 29, 2016 issued in EP 13844083.9.
Ping, Z. et al., "Research and application of magnetic fluidized bed", Chemical Industry and Engineering Progress, (Apr. 25, 2006), pp. 371-377, with English absttract.

(Continued)

*Primary Examiner* — Monica A Shin
(74) *Attorney, Agent, or Firm* — Kaplan IP Law, P.C.; Jonathan M. Kaplan

(57) ABSTRACT

The present invention provides compositions and methods for reducing bacterial contamination or infection in plants, animals, fabrics, and products therefrom. The present invention also provides compositions and methods for reducing human infections and the emergence of antibiotic resistance. In particular, the invention provides magnetic nanoparticles comprising bactericidal or bacteriostatic enzymes in one component, substrates for the enzymes in a second component, and a bactericidal chemical agent that works in combination or synergistically with the enzymes. The compositions are dormant and become active upon exposure to hydration, oxygen, or mixing.

17 Claims, 12 Drawing Sheets

(56) References Cited

U.S. PATENT DOCUMENTS

| | | |
|---|---|---|
| 10,260,061 B2 | 4/2019 | Corgie |
| 10,316,313 B2 | 6/2019 | Corgie |
| 10,351,841 B2 | 7/2019 | Corgie |
| 2003/0138490 A1 | 7/2003 | Hu et al. |
| 2003/0146529 A1 | 8/2003 | Chen et al. |
| 2003/0203056 A1 | 10/2003 | Tumbers |
| 2004/0039201 A1 | 2/2004 | Lugade et al. |
| 2004/0043135 A1 | 3/2004 | Han et al. |
| 2004/0166547 A1 | 8/2004 | Sullivan et al. |
| 2006/0034816 A1* | 2/2006 | Davis ............... A61L 15/60 424/94.4 |
| 2006/0127461 A1* | 6/2006 | Bloor ............... A61L 15/38 424/445 |
| 2006/0165910 A1 | 7/2006 | Kodas et al. |
| 2006/0286379 A1 | 12/2006 | Gao et al. |
| 2006/0289354 A1* | 12/2006 | Zhou ............... A01N 63/02 210/601 |
| 2007/0135312 A1 | 6/2007 | Melbouci |
| 2007/0154565 A1 | 7/2007 | Zaghmout |
| 2008/0103061 A1 | 5/2008 | Lugade et al. |
| 2008/0287288 A1 | 11/2008 | Ying et al. |
| 2008/0305048 A1 | 12/2008 | Josephson et al. |
| 2009/0053512 A1 | 2/2009 | Pyun et al. |
| 2009/0142281 A1 | 6/2009 | Rand et al. |
| 2009/0214885 A1 | 8/2009 | Her et al. |
| 2009/0238811 A1 | 9/2009 | McDaniel et al. |
| 2009/0285890 A1 | 11/2009 | Plas et al. |
| 2010/0056360 A1 | 3/2010 | Lee |
| 2010/0056816 A1 | 3/2010 | Wallin et al. |
| 2010/0152326 A1 | 6/2010 | Kurz |
| 2010/0226856 A1 | 9/2010 | Vitaliano et al. |
| 2010/0285376 A1 | 11/2010 | Hsueh et al. |
| 2011/0203756 A1 | 8/2011 | Nordin et al. |
| 2011/0300201 A1 | 12/2011 | Becker et al. |
| 2011/0312497 A1 | 12/2011 | Barg et al. |
| 2012/0039799 A1 | 2/2012 | Franzen et al. |
| 2012/0058074 A1 | 3/2012 | Braig et al. |
| 2012/0108491 A1 | 5/2012 | Simonsen |
| 2012/0123026 A1 | 5/2012 | Lugade et al. |
| 2012/0214218 A1 | 8/2012 | Xing et al. |
| 2012/0270031 A1 | 10/2012 | Guan et al. |
| 2013/0196407 A1 | 8/2013 | Sheldon et al. |
| 2014/0004583 A1 | 1/2014 | Corgie et al. |
| 2014/0046023 A1 | 2/2014 | Gottschall et al. |
| 2014/0100111 A1* | 4/2014 | Schultz, Sr. ...... C09D 105/08 504/140 |
| 2014/0296507 A1 | 10/2014 | Sannino et al. |
| 2014/0377789 A1 | 12/2014 | Moerman |
| 2015/0056145 A1 | 2/2015 | Chae et al. |
| 2015/0252352 A1* | 9/2015 | Corgie ............... A62D 3/02 210/606 |
| 2017/0096658 A1 | 4/2017 | Corgie et al. |
| 2017/0175101 A1 | 6/2017 | Corgie et al. |
| 2017/0189960 A1 | 7/2017 | Ibe |
| 2018/0087043 A1 | 3/2018 | Corgie |
| 2018/0146663 A1 | 5/2018 | Corgie |
| 2018/0200701 A1 | 7/2018 | Corgie |
| 2019/0174745 A1 | 6/2019 | Corgie |
| 2019/0174746 A1 | 6/2019 | Corgie |
| 2019/0309282 A1 | 10/2019 | Corgie |
| 2020/0315167 A1 | 10/2020 | Corgie |
| 2020/0330967 A1 | 10/2020 | Corgie |

FOREIGN PATENT DOCUMENTS

| | | |
|---|---|---|
| CN | 101198255 A | 6/2008 |
| CN | 102329008 A | 1/2012 |
| CN | 102329008 B | 1/2013 |
| CN | 103675115 A | 3/2014 |
| CN | 104624166 A | 5/2015 |
| CN | 104624166 B | 6/2017 |
| EP | 1028628 A1 | 8/2000 |
| EP | 1028628 B1 | 2/2003 |
| EP | 2110175 A1 | 10/2009 |
| EP | 2593544 A2 | 5/2013 |
| EP | 1476753 B1 | 8/2013 |
| GB | 2211504 A | 7/1989 |
| JP | 2002128618 A | 5/2002 |
| JP | 2005532533 A | 10/2005 |
| JP | 2008543850 A | 12/2008 |
| JP | 4598403 B2 | 12/2010 |
| KR | 2011/033575 A | 3/2011 |
| SU | 1000098 | 2/1983 |
| WO | 8802600 A1 | 4/1988 |
| WO | 9111105 A1 | 8/1991 |
| WO | 95/012392 A1 | 5/1995 |
| WO | 199715664 A1 | 5/1997 |
| WO | 9922597 A1 | 5/1999 |
| WO | WO9922597 A1 | 5/1999 |
| WO | 0158267 A1 | 8/2001 |
| WO | 2003084982 A2 | 10/2003 |
| WO | WO03080796 A2 | 10/2003 |
| WO | WO2006004557 A1 | 1/2006 |
| WO | 2006138271 A1 | 12/2006 |
| WO | 2008156948 A2 | 12/2008 |
| WO | WO2009115335 A1 | 9/2009 |
| WO | 2011161261 A1 | 12/2011 |
| WO | 2012010295 A1 | 1/2012 |
| WO | 2012023847 A2 | 2/2012 |
| WO | 2012122437 A2 | 9/2012 |
| WO | WO2012122437 A2 | 9/2012 |
| WO | WO2012122437 A3 | 9/2012 |
| WO | 2013046165 A1 | 4/2013 |
| WO | WO2013109057 A1 | 7/2013 |
| WO | 2013170050 A1 | 11/2013 |
| WO | 2014055853 A1 | 4/2014 |
| WO | 2014083048 A1 | 6/2014 |
| WO | WO2015078241 A1 | 6/2015 |
| WO | WO-2015100432 A2 * | 7/2015 |
| WO | WO2015111030 A2 | 7/2015 |
| WO | WO2015113047 A2 | 7/2015 |
| WO | WO2015145222 A2 | 10/2015 |
| WO | WO2015157530 A2 | 10/2015 |
| WO | 2016138477 A1 | 9/2016 |
| WO | 2016186879 A1 | 11/2016 |
| WO | 2017011292 A1 | 1/2017 |
| WO | 2017180383 A1 | 10/2017 |
| WO | 2018034877 A1 | 2/2018 |
| WO | WO2018102319 A1 | 6/2018 |
| WO | 2020051159 A1 | 3/2020 |
| WO | 2020069227 A1 | 4/2020 |

OTHER PUBLICATIONS

Chinese Office Action dated Mar. 23, 2016 issued in corresponding Chinese Patent Application No. 201380063389.8 with English-language translation.

Abdullah M. et al., "Preparation of Oxide Particles with Ordered Macropores by Colloidal Templating and Spray Pyrolysis", Acta Materialia 52:5151-5156 (2004).

Davis, M. et al., "Formation of Three-Dimensional Ordered Hierarchically Porous Metal Oxides Vi Hybridized Epoxide Assisted/Colloidal Templating Approach", ACS Applied Materials & Interfaces 5:7786-7792 (2013).

Niu T. et al., "Preparation of Meso-Macroporous alpha-Alumina Using Carbon Nanotube as the Template for the Mesopore and Their Application to the Preferential Oxidation of CO in H2-Rich Gases", J Porous Mater 20:789-798 (2013).

Seelan S. et al., "Macroporous Ceramics Coated With Mesoporous Layer for Enzyme Encapsulation", Key Engineering Materials 317-318: 717-722 (2006).

Veitch N.C., "Horseradish Peroxidase: A Modern View of a Classic Enzyme", Phytochemistry 65:249-259 (2004).

Yang L. et al., "Robust Macroporous Materials of Chiral Polyaniline Composites", Chem. Mater. 18(2): 297-300 (2006).

Kim, M. et al., Colorimetric Quantification of Galactose Using a Nanostructured Multicatalyst System . . . Analyst 137(5)1137-1143, 2012.

Lee J. et al., Magnetically Separable and Highly Stable Enzyme System Based on Crosslinked Enzyme Aggregates Shipped in

(56) References Cited

OTHER PUBLICATIONS

Magnetite Coated Mesoporous Silica J of Materials Chemistry 19(42)864-70, 2009.

Extended European Search Report dated Oct. 8, 2018 issued in EP Application No. 16796938.5.

Boone, Christopher D. et al. "Carbonic Anhydrase: An Efficient Enzyme with Possible Global Implications," International Journal of Chemical Engineering, vol. 2013, Article ID 813931, 2013.

Caswell, Jill M. et al. "From P450 Discovery to Scale-Up for Delivery of Chiral Intermediates," Department of Biocatalysisand Isotope Chemistry, Almac Sciences, UK, downloaded from https://www.almacgroup.com in 2015.

Duong, The-Phong et al. "Characterization of Mechanical Properties of Magnetite-polymer Composite Films," Proceedings of the XIth International Congress and Exposition, Jun. 2-5, 2008 Orlando, Florida USA.

Hoffmann, Sandra et al. "Annual Cost of Illness and Quality-Adjusted Life Year Losses in the United States Due to 14 Foodborne Pathogens," Journal of Food Protection, vol. 75, No. 7, pp. 1292-1302, 2012.

Kim, J. et al. A magnetically separable, highly stable enzyme system based on nanocomposites of enzymes and magnetic nanoparticles shipped in hierarchically ordered, mesocellular, mesoporous silica. Small. 2005. vol. 1. No. 12. pp. 1203-1207.

Kirkman, Henry N. et al. "Catalase: A tetrameric enzyme with four tightly bound molecules of NADPH," Proc. Natl. Acad. Sci. USA, vol. 81, pp. 4343-4347, Jul. 1984.

McCall, Keith A. et al. "Function and Mechanism of Zinc Metalloenzymes," American Society for Nutritional Sciences, 1437S-1446S, 2000.

Mix, Stefan. "Shortening the Path—Pharmaceutical Materials from Enzymatic Reactions," Almac Group, Organic Process Research & Development Prague, Oct. 17-19, 2016.

PCT International Preliminary Report on Patentability dated Jul. 31, 2017 for PCT/US2016/041461 filed on Jul. 8, 2016, 10 pages.

PCT International Preliminary Report on Patentability dated Nov. 21, 2017 for PCT/US2016/031419 filed on May 9, 2016, 8 pages.

PCT Search Report and Written Opinion dated Jul. 27, 2016 for PCT/US2016/031419 filed on May 9, 2016, 16 pages.

PCT Search Report and Written Opinion dated Jul. 3, 2017 for PCT/US2017/026086 filed on Apr. 5, 2017, 22 pages.

PCT Search Report and Written Opinion dated Oct. 25, 2017 for PCT/US2017/045655 filed on Aug. 6, 2017, 12 pages.

PCT Search Report and Written Opinion dated Sep. 16, 2016 for PCT/US2016/041461 filed on Jul. 8, 2016, 11 pages.

Porter, Michael M. et al. "Biomimetic Materials by Freeze Casting," JOM: the journal of the Minerals, Metals, and Materials Society, 65(6), Apr. 2013.

Sawayama, Andrew M. et al. "A Panel of Cytochrome P450 BM3 Variants to Produce Drug Metabolites and Diversify Lead Compounds," Chem. Eur. J. 2009.

Wainaina, James et al. "Synthesis of Magnetite/Amphiphilic Polymer Composite Nanoparticles as Potential Theragnostic Agents," Journal of Nanoscience and Nanotechnology, vol. 12, 5920-5924, 2012.

Yamagata, Mika et al. "Magnetite/Polymer Composite Particles Prepared by Molecular Assembling Followed by In-Situ Magnetite Formation," Macromol. Symp., 245-246, 363-370, 2006.

PCT Search Report and Written Opinion dated Feb. 12, 2018 for PCT/US2017/063542 filed on Nov. 28, 2017, 9 pages.

El-Zahab et al. "Enabling multienzyme biocatalysis using nanoporous materials," Biotechnol Bioeng, vol. 87, No. 2, pp. 178-183, Jul. 20, 2004.

Liu et al. "Nanoparticle-supported multi-enzyme biocatalysis with in situ cofactor regeneration," J Biotechnol, vol. 139, No. 1, pp. 102-107, Oct. 19, 2008.

Petkova et al. "Synthesis of silica particles and their application as supports for alcohol dehydrogenases and cofactor immobilizations: conformational changes that lead to switch in enzyme stereoselectivity," Biochim Biophys Acta, vol. 1824, No. 6, pp. 792-801, Mar. 26, 2012.

Zheng et al. "Magnetic field intensified bi-enzyme system with in situ cofactor regeneration supported by magnetic nanoparticles," J Biotechnol, vol. 168, No. 2, pp. 212-217, Jun. 10, 2013.

Carozza, Susan E. et al. "Risk of Childhood Cancers Associated with Residence in Agriculturally Intense Areas in the United States," Environ. Health Perspect. 116(4):559-65 (2008).

Corning, Website at https://www.corning.com/worldwide/en/products/life-sciences/products/adme-tox-research/recombinant-metabolic-enzymes.html. Downloaded Mar. 4, 2018.

Cypex, Website located at http://www.cypex.co.uk/ ezcypbuf.htm. Dowloaded on Mar. 4, 2018.

Cytochrome c Oxidase Assay Kit, Sigma-Aldrich 2014:1-4; website located at https://www.ncbi.nlm.nih.gov/pmc/articles/PMC2884625/. Downloaded on Mar. 4, 2018.

Gong, Jin-Song et al., "Nitrilases in nitrile biocatalysis: recent progress and forthcoming research," Microbial Cell Factories 11(1):142 (2012).

Kerr, Susan. "Drying-Off Lactating Livestock," Small Farms vol. V, No. 3 (2010).

Kirkman, Henry N. et al. "Catalase: A tetrameric enzyme with four tightly bound molecules of NADPH," Proc. Natl. Acad. Sci. USA. 81(14):4343-7 (1984).

Li, Yi et al. "Rapid Kinetic Microassay for Catalase Activity," J. Biomolecular Techniques 18(4):185-187 (2007).

Mark, Genevieve L. et al. "Molecular-based strategies to exploitPseudomonas biocontrol strains forenvironmental biotechnologyapplications," FEMS Microbiol. Ecol. 56(2):167-77 (2006).

Newsholme, Philip et al. "Glutamine and glutamate—their central role in cell metabolism and function," Cell Biochem. and Function, 21:1-9 (2003).

Nielsen, Christel. "Economic Impact of Mastitis in Dairy Cows," Department of Animal Breeding and Genetics, Uppsala, Sweden, Swedish University of Agricultural Sciences (2009).

Purdy, Michael A. et al. "Effect of Growth Phase and Cell Envelope Structure on Susceptibility of *Salmonella typhimurium* to the Lactoperoxidase-Thiocyanate-Hydrogen Peroxide System," Infection and Immunity, 39(3), 1187-1195 (1983).

Reeves, Margaret et al. "Greater Risks, Fewer Rights: U.S. Farmworkers and Pesticides," Int'l J., Occup. Environ. Health 9(1):30-39 (2003).

Reiter, Bruno et al. "Nonspecific Bactericidal Activity of the Lactoperoxidase-Thiocyanate-Hydrogen Peroxide System of Milk Against *Escherichia coli* and Some Gram-Negative Pathogens," Infection and Immunity, 13(3), 800-807 (1976).

Sigma Chemical Corporation and Kessey, J. (1994) Enzymatic Assay of Choline Oxidase (EC 1.13.17). https://www.sigmaaldrich.com/content/dam/sigma-aldrich/docs/Sigma/Enzyme_Assay/c5896enz.pdf.

Smith, Temple F. et al. "Comparison of Biosequences," Adv. Appl. Math. 2:482-489 (1981).

Tang, Cuyue et al. "Major Role of Human Liver Microsomal Cytochrome P450 2C9 (CYP2C9) in the Oxidative Metabolism of Celecoxib, a Novel Cyclooxygenase-II Inhibitor," J. Pharm. Exp. Therap., 293(2):453-459 (2000).

Trefzer, Axel et al. "Biocatalytic Conversion of Avermectin to 4"-Oxo-Avermectin: Improvement of Cytochrome P450 Monooxygenase Specificity by Directed Evolution," Appl. Environ. Microbiol. 73(13):4317-4325 (2007).

Wilbur, Karl M. et al. "Electrometric and Colorimetric Determination of Carbonic Anhydrase," J. Biol. Chem. 176:147-154 (1948).

Xia, Menghang et al. "Compound Cytotoxicity Profiling Using Quantitative High-Throughput Screening," Environmental Health Perspectives, 116(3):284-291 (2008).

Zhu, Mingshe et al. "Cytochrome P450 3A-Mediated Metabolism of Buspirone in Human Liver Microsomes," Drug Metabolism and Disposition 33(4):500-507 (2005).

World Health Day, Combat Drug Resistance: No Action Today Means No Cure Tomorrow, Statement by WHO Director-General,

(56) References Cited

OTHER PUBLICATIONS

Dr. Margaret Chan, Apr. 6, 2011, http://www.who.int/mediacentre/news/statements/2011/whd_20110407/en/. Downloaded Mar. 4, 2018.
Antibiotic Resistance Threats in the United States, 2013, Centers for Disease Control and Prevention: Atlanta, GA, http://www.cdc.gov/drugresistance/threat-report-2013/. Downloaded Mar. 4, 2018.
Roberts, Rebecca R. et al. "Hospital and Societal Costs of Antimicrobial-Resistant Infections in a Chicago Teaching Hospital: Implications for Antibiotic Stewardship," Clin. Infect. Dis. 49(8):1175-84 (2009).
Hoffmann, S. et al. Making Sense of Recent Cost-of-Foodborne-Illness Estimates, United States Department of Agriculture, Economic Research Service, 2013, http://www.ers.usda.gov/publications/eib-economic-information-bulletin/eib118.aspx. Downloaded Mar. 4, 2018.
U.S. Department of Health and Human Services Food and Drug Administration Center for Drug Evaluation and Research (CDER)"Safety Testing of Drug Metabolites Guidance for Industry", Nov. 2016.
MeSH Lactoperoxidase information downloaded Oct. 1, 2018 at https://lwww.ncbi.nlm.nih.gov/mesh/?term=lactoperoxidase.
Corgie et al. "Self-Assemblies of Magnetic Nanoparticles (MNPs) and Peroxidase Enzymes: Mesoporous Structures and Nanoscale Magnetic Field Effects (nano-MFEs) for Enhanced Activity BioNanoCatalysts (BNCs)"; Cleantech, www.ct-si.org; Dec. 2012.
Hielscher, Thomas. "Ultrasonic production of nano-size dispersions and emulsions," ENS 05, Paris, France, XP-002788816, Dec. 2005.
Lee et al. "Microfluidic continuous magnetophoretic protein separation using nanoparticle aggregates," Microfluidics and Nanofluidics, Springer, Berlin, DE, vol. 11, No. 4, May 2011.
Ahmad et al., Physico-Chemical Processes. Water Environment Research, vol. 77, No. 6, Literature Reviews {CD-ROM content}, pp. 982-1156 (2005).
Adams et al. Specificity of Glucose Oxidase. Archives of Biochemistry and Biophysics 91 (1960) 230-234.
Ansari et al. Potential applications of enzymes immobilized on/in nano materials: A review. Biotechnology Advances 30 (2012) 512-523.
Anthon et al. Colorimetric Method for the Determination of Lipoxygenase Activity. J. Agric. Food Chem. 49 (2001) 32-37.
Banerjee et al. A High-Throughput Colorimetric Assay for Enantioselective Screening of Nitrilase-Producing Microorganisms Using pH Sensitive Indicators. Journal of Biomolecular Screening 8(5); 2003, pp. 559-565.
Baskar et al., Magnetic immobilization and characterization of beta-amylase as nanobiocatalyst for hydrolysis of sweet potato starch. Biochemical Engineering Journal 102 (2015) 18-23.
Cassimjee. ω-Transaminase in Biocatalysis Methods. ractions and Engineering. Doctoral Thesis KTH Royal Institute of Technology, School of Biotechnology Stockholm (2012).
Dong et al. Efficient biosynthesis of uridine diphosphate glucose from maltodextrin by multiple enzymes immoblized on magnetic nanoparticles. Carbohydrate Research 345, (2010) 1622-1626.
Errede et al. Oxidation of ferrocytochrome c by mitochondrial cytochrome c oxidase. Proc. Nat. Acad. Sci. USA, vol. 73, No. 1, pp. 113-117, Jan. 1976.
Gebreyohannes et al. Nanoscale tuning of enzyme localization for enhanced reactor performance in a novel magnetic-responsive biocatalytic membrane reactor. Journal of Membrane Science 487 (2015) 209-220.
Illanes et al. Recent trends in biocatalysis engineering. Bioresource Technology 115 (2012) 48-57.
Karn et al. Nanotechnology and in Situ Remediation: A Review of the Benefits and Potential Risks. Environmental Health Perspectives, vol. 117, No. 12 (Dec. 2009), pp. 1823-1831.
Khan et al. Hazardous Waste Treatment Technologies. Water Environment Research, vol. 79, No. 10, Literature Reviews [CD-ROM content] (2007), pp. 1858-1902.
Kim et al. Hazardous Waste Treatment Technologies. Water Environment Research, vol. 64, No. 4, 1992: Literature Review (Jun. 1992), pp. 469-479.
Kim et al. Single enzyme nanoparticles in nanoporous silica: A hierarchical approach to enzyme stabilization and immobilization. Enzyme and Microbial Technology 39 (2006) 272-480.
Kim et al. Nanobiocatalysis and its potential applications. Trends in Biotechnology vol. 26, No. 11 (2008) 639-646.
Neto. Process Considerations for the Asymmetric Synthesis of Chiral Amines using w-Transaminase. Thesis, center for Process Engineering and Technology Department of Chemical and Biochemical Engineering Technical University of Denmark, Aug. 2013, pp. 1-108 and 109-117.
Rai et al. Optimization for production of liquid nitrogen fertilizer from the degradation of chicken feather by iron-oxide (Fe3O4) magnetic nanoparticles couples β-keratinase. Biocatalysis and Agricultural Biotechnology, vol. 4, Issue 4, Oct. 2015, pp. 1-13.
Sanders et al., Self-Assembly Using Dynamic Combinatorial Chemistry. Philosophical Transactions: Mathematical, Physical and Engineering Sciences, vol. 362, No. 1819, Organizing Atoms: Manipulation of Matter on the Sub-10 nm Scale (Jun. 15, 2004) pp. 1239-1245.
Sheldon et al. Enzyme immobilisation in biocatalysis: why, what and how. Chem. Soc. Rev. 2013, vol. 42, 6223-6225.
Tappel et al. E. Lipoxidase. H. F. Linskens et al. (eds.) Modern Methods of Plant Analysis/Moderne Methoden der Pflanzenanalyse Springer-Verlag OHG. Berlin—Goettingen—Heidelberg 1964—pp. 469-471.
Tundo et al. methods and Reagents for Green Chemistry: An Introduction. 2007. A John Wiley & Sons Inc. Publication, pp. 1-312 (333 pages total).
Villaverde et al. Hydroperoxide production from linoleic acid by heterologous Gaeumannomyces graminis tritici ipoxygenase: Optimization and scale-up. Chemical Engineering Journal 214 (2013) 82-90.
Villaverde et al. Analysis of linoleic acid hydroperoxides generated by biomimetic and enzymatic systems through an integrated methodology. Industrial Crops and Products 34 (2011) 1474-1481.
Wang et al. Enhanced phenol degradation in coking wastewater by immobilized laccase on magnetic mesoporous silica nanoparticles in a magnetically stabilized fluidized bed. Bioresource Technology 110 (2012) 120-124.
Wilson et al. Glucose oxidase: an ideal enzyme. Biosensors and Bioelectronics 7 (1992) 165-185.
Zheng et al. Effect of molecular mobility on coupled enzymatic reactions involving cofactor regeneration using nanoparticle-attached enzymes Journal of Biotechnology 154 (2011) 274-280.
The Journal Record News Briefs: Feb. 15, 2010, The Journal Record (Oklahoma City, OK) Feb. 15, 2010 Monday, pp. 1-5.
Three better ways to upcycle waste oil; NUS researchers offer cheaper, greener methods to produce biodiesel the Straits Times (Singapore), Apr. 18, 2015 Saturday, pp. 1-2.
English abstract only of International Application No. WO 03/084982.
Chinese Office Action dated Apr. 28, 2015 received from Application No. 201280022702.9, together with an English-language translation.
Azevedo A.M. et al., "Horseradish Peroxidase: A Valuable Tool in Biotechnology", Biotechnology Annual Review 9:199-247 (2003).
Chalkias N.G. et al., "Activity Increase of Horseradish Peroxidase in the Presence of Magnetic Particles", J. Am. Chem. Soc. 130:2910-2911 (2008).
Corgie S.C. et al., Self-Assembled Complexes of Horseradish Peroxidase with Magnetic Nanoparticles Showing Enhanced Peroxidase Activity, Advanced Functional Materials 22:1940-1951 (Feb. 15, 2012).
Corvini P.F.X. et al., "Lance: Laccase-Nanoparticle Conjugates for the Elimination of Micropollutants (Endocrine Disrupting Chemicals) from Wastewater in Bioreactors", Rev Environ Sci Biotechnol 9:23-27 (2010).
Huang J. et al., "Zinc Tetraaminophthalocyanine-Fe3O4 Nanoparticle Composite for Laccase Immobilization", International Journal of Nanomedicine 2(4): 775-784 (2007).
Luo X-L et al., "Electrochemically Deposited Chitosan Hydrogel for Horseradish Peroxidase Immobilization Through Gold Nanoparticles Self-Assembly", Biosensors and Bioelectronics 21:190-196 (2005).

(56) References Cited

OTHER PUBLICATIONS

Tang D. et al., "Direct Electrochemical Immunoassay Based on Immobilization of Protein-Magnetic Nanoparticle Composites on to Magnetic Electrode Surfaces by Sterically Enhanced Magnetic Field Force", Biotechnology Letters 28:559-565 (2006).
Wang F. et al., "Magnetic Mesoporous Silica Nanoparticles: Fabrication and Their Laccase Immobilization Perforamnce", Bioresource Technology 101:8931-8935 (2010).
Yang H-H et al., "Magnetite-Containing Spherical Silica Nanoparticles for Biocatalysis and Bioseparations", Analytical Chemistry 76(5): 1316-1321 (Mar. 1, 2004).
International Search Report dated Oct. 10, 2012 received from the Korean Intellectual Property Office from related Application No. PCT/US2012/028392.
International Search Report dated Feb. 20, 2014 received from the Russian Patent Office from related Application No. PCT/US2013/063441.
Morrison et al. Peroxidase-catalyzed halogenation. Annual Review of Biochemistry, vol. 45, 861-888, 1976.
Aguila, Sergio et al. "Stereoselective oxidation of R-(+)-limonene by chloroperoxidase from Caldariomyces fumago," Green Chemistry 10(52):647-653 (2008).
Altschul, Stephen F. et al. "Basic Local Alignment Search Tool," J. Mol. Biol. 215:403-410 (1990).
Banerjee, Anirban et al. "A rapid and sensitive fluorometric assay method for the determination of nitrilase asctivity," Biotechnol. Appl. Biochem. 37(3):289-293 (2003).
Betancor, Lorena et al. "Preparation of a Stable Biocatalyst of Bovine Liver Catalase Using Immobilization and Postimmobilization Techniques," Biotechnology Progress 19(3):763-767 (2003).
Chau, Yat-Pang et al. "Differential permeability of blood microvasculatures in various sympathetic ganglia of rodents," Anatomy and Embryology, 194(3):259-269 (1996).
Corgie, Stephane et al. "Universal enzyme immobilisation within hierarchically-assembled magnetic scaffolds," Chem. Today 34(5):15-20 (2016).
Dadashipour, Mohammad et al. "Hydroxynitrile Lyases: Insights into Biochemistry, Discovery, and Engineering," ACS Catal. 1:1121-49 (2011).
Denisov, Llia et al. "Structure and Chemistry of Cytochrome P450," Chem. Rev. 105(6):2253-77 (2005).
Dresser, George K. et al. "Pharmacokinetic-Pharmacodynamic Consequences and Clinical Relevance of Cytochrome P450 3A4 Inhibition," Clinical Pharmacokinetics 38(1):41-57 (2012).
Duan, Xiaonan et al. "Hierarchical Hybrid Peroxidase Catalysts for Remediation of Phenol Wastewater," ChemPhysChem, 15(5):974-980 (2014).
Fiers, W. et al., "Complete nucleotide sequence of SV40 DNA," Nature 273: 113-120 (1978).
Glieder, Anton et al. "Comprehensive Step-by-Step Engineering of an (R)-Hydroxynitrile Lyase for Large-Scale Asymmetric Synthesis**," Angew. Chem. Int. Ed. 42:4815 (2003).
Greenaway, P.J. et al. "Human cytomegalovirus DNA: BumHI, EcoRI and Pst I restriction endonuclease cleavage maps," Gene 18: 355-360 (1982).
Gupta, Namita et al. "Simplified para-nitrophenyl palmitate assay for lipases and esterases," Analytical Biochemistry 311:98-99 (2002).
Hess, B. et al. "Cooperation of Glycolytic Enzymes," J. Adv. Enzyme Res. 7:149 (1968).
Hitzeman, Ronald A. et al., "Isolation and Characterization of the Yeast 3-Phosphoglycerokinase Gene (PGK) by an Immunological Screening Technique*," J. Biol. Chem. 255:2073 (1980).
Holland, Michael J. et al., "Isolation and Identification of Yeast Messenger Ribonucleic Acids Coding for Enolase, Glyceraldehyde-3-phosphate Dehydrogenase, and Phosphoglycerate Kinase," Biochemistry 17:4900 (1978).
Iribarne, Christelle et al. "Involvement of Cytochrome P450 3A4 Enzyme in the N-Demethylation of Methadone in Human Liver Microsomes," Chem. Res. Tox. 9(2): p. 365-373 (1996).

Jones, G.M. et al. "Environmental Streptococcal and Coliform Mastitis," Virgina Cooperative Extension, Publ. 404-234, 2009.
Jones, G.M. "Understanding the Basics of Mastitis," Virgina Cooperative Extension, Publ. 404-233, 2009.
Joo, Hyun et al. "Laboratory evolution of peroxide-mediated cytochrome P450 hydroxylation," Nature, 399(6737):670-673 (1999).
Kim, H. et al. "Cytochrome P450 isozymes responsible for the metabolism of toluene and styrene in human liver microsomes," Xenobiotica 27(7):657-665 (1997).
Kusumoto, I. "Industrial Production of L-Glutamine," American Society for Nutritional Sciences, 131:2552S-2555S (2001).
Lindskog et al. The catalytic mechanism of mammalian carbonic anhydrases New Horizons 7:175-95 (2000).
Lucas, John A. et al. "The Evolution of Fungicide Resistance," Advances in Applied Microbiology, vol. 90, 2015.
Mathew, Sam et al. "ω-Transaminases for the Production of Optically Pure Amines and Unnatural Amino Acids," ACS Catalysis 2(6):993-1001 (2012).
Moses, Marion. "Pesticide-Related Health Problems and Farmworkers," AAOHN J., 37(3):115-30 (1989).
Needleman, Saul B. et al. "A General Method Applicable to the Search for Similarities in the Amino Acid Sequence of Two Proteins," J. Mol. Biol. 48:443 (1970).
Pearson, William R. et al. "Improved tools for biological sequence comparison," Proc. Natl. Acad. Sci. vol. 85, pp. 2444-2448, Apr. 1988.
Ritter, L. et al. "Addressing the Linkage between Exposure to Pesticides and Human Health Effects—Research Trends and Priorities for Research," J. Tox. Environ. Health 9(6):441-56 (2006).
Sawayama, Andrew M. et al. "A Panel of Cytochrome P450 BM3 Variants to Produce Drug Metabolites and Diversify Lead Compounds," Chemistry 15(43):11723-9 (2009).
Schätzle, Sebastian et al. "Rapid and Sensitive Kinetic Assay for Characterization of ω-Transaminases," Analytical Chemistry 81(19):8244-8248 (2009).
Shaw, Nicholas M. et al. "Lonza: 20 Years of Biotransformations," Adv. Synth. and Catalysis 345(4): 425-435 (2003).
Shingles, Richard et al. "Direct Measurement of ATP-Dependent Proton Concentration Changes and Characterization of a K+-Stimulated ATPase in Pea Chloroplast Inner Envelope Vesicles," Plant Physiol. 106(2):731-737 (1994).
Shingles, Richard et al. "Measurement of Carbonic Anhydrase Activity Using a Sensitive Fluorometric Assay," Analytical Biochemistry 252(1):190-197 (1997).
Sorouraddin, M.H. et al. "Spectrophotometric determination of some catecholamine drugs using sodium bismutha," Journal of Pharmaceutical and Biomedical Analysis 18:877-881 (1998).
Tsotsou, Georgia E. et al. "High throughput assay for cytochrome P450 BM3 for screening libraries of substrates and combinatorial mutants," Biosensors & Bioelectronics, 17:119-131 (2002).
Wan, Feng-Yi et al. "The influence of oxidation of membrane thiol groups on lysosomal proton permeability," Biochemistry Journal, 360, 355-362 (2001).
Welk, A. et al. "Microbicidal efficacy of thiocyanate hydrogen peroxide after adding lactoperoxidase under saliva loading in the quantitative suspension test," Archives of Oral Biology, 56:1576-1582 (2011).
Wells, Andrew. "What Is in a Biocatalyst?," Organic Process Res. Dev. 10:678-681 (2006).
Wrighton, Steven A. et al. "The Human Hepatic Cytochromes P450 Involved in Drug Metabolism," Crit. Rev. Tox. 22(1):1-21 (1992).
Yamazaki, Hiroshi et al., "Roles of Cytochromes P450 1A2 and 3A4 in the Oxidation of Estradiol and Estrone in Human Liver Microsomes," Chem. Res. Tox. 11(6): p. 659-665 (1998).
U.S. Appl. No. 62/163,032, filed May 18, 2015.
U.S. Appl. No. 62/193,041, filed Jul. 15, 2015.
U.S. Appl. No. 62/323,663, filed Apr. 16, 2016.
Bhosale, S. et al., "Molecular and Industrial Aspects of Glucose Isomerase," Microbiol. Rev. 60(2):280-300 (1996).
Bosch, E.H. et al., "The lactoperoxidase system: the influence of iodide and the chemical and antimicrobial stability over the period of about 18 months," J. Applied Microbiol., 89(2), 215-24 (2000).

(56) References Cited

OTHER PUBLICATIONS

Alexander et al. "Cytochrome P450 (E.C. 1.14.–.–)bph_506_108a 215," Br. J. Pharmacol. 158(Suppl 1): S215-S217 (2009).
Bradford, Marion M. "A Rapid and Sensitive Method for the Quantitation of Microgram Quantities of Protein Utilizing the Principle of Protein-Dye Binding," Analytical Biochemistry, 72(1-2):248-254 (1976).
Demirel, D. et al. Preparation and characterization of magnetic duolite-polystyrene composite particles for enzyme immobilization, Journal of Food Engineering, 62(2004)203-208.
European Search Report for European application No. 17782855.5 dated Nov. 11, 2019.
PCT Search Report and Written Opinion dated Dec. 23, 2019 for PCT/US19/49397.
PCT Search Report and Written Opinion dated Dec. 11, 2019 for PCT/US19/53307.
Zheng, M. et al. "Magnetic field intensified bi-enzyme system with in situ cofactor regeneration . . . "Journal of Biotechnology vol. 168 No. 2 (Oct. 2013).
Pecova, M. et al. "Thermostable trypsin conjugates immobilized to biogenic magnetite show a high operational stability and remarkable reusability for protein digestion," Nanotechnology 2013 vol. 2013 125102 pp. 1-11.
Hydrolase Nomenclature excerpt from Enzyme Nomenclature Recommendations Nomenclature Committee of the International Union of Biochemistry and Molecular Biology download from https://www.qmul.ac.uk/sbcs/iubmb/enzyme/EC3/ on Nov. 22, 2019.

* cited by examiner

Nematode cyst experiment

Nematode egg experiment

MAGNETICALLY IMMOBILIZED BIOCIDAL ENZYMES AND BIOCIDAL CHEMICALS

CROSS REFERENCE TO RELATED APPLICATIONS

This application is a Continuation Application of PCT/US17/45655 filed Aug. 6, 2017 and claims the benefit of U.S. Provisional Application No. 62/374,836, filed on Aug. 13, 2016 and 62/511,331, filed on May 25, 2017, each of which are incorporated herein by reference in their entirety.

FIELD OF THE INVENTION

The present invention provides compositions and methods for reducing microbial and nematodal contamination or infection in plants, animals, fabrics, and products therefrom. The present invention also provides compositions and methods for reducing human infections and the emergence of antimicrobial resistance. In particular, the invention provides magnetic nanoparticles comprising biocidal or biostatic enzymes in one component, substrates for the enzymes in a second component, and a biocidal chemical agent that works in combination or synergistically with the enzymes. The compositions are dormant and become active upon exposure to hydration, oxygen, or mixing.

BACKGROUND OF THE INVENTION

Contaminating and infectious microorganisms significantly reduce the yield, quality, and safety of agricultural and animal products worldwide. The resulting economic losses are in the hundreds of billions of dollars annually in the United States alone. In addition, current methods for reducing plant and animal infections rely heavily on the use of antimicrobial chemicals that may result in fungicide and antibiotic resistance that, in turn, increases the probability of selecting for drug-resistant plant, animal, and human pathogens. These microbes have been selected to survive in the presence of medically and agriculturally important antimicrobial chemicals and are a significant threat to human health and food security.

For example, Antibiotic Resistant Microbes (ARM) are a growing public health concern because infections have become increasingly difficult and expensive to treat. Concern turns into crisis in hospital environments. Antibiotics of last resort such as vancomycin, are steadily becoming ineffectual against superstrains. Carbapenem Resistant Enterobacteriaceae (CRE), some of the most ubiquitous microbes in the environment, are now resistant to almost all antibiotics. CRE infections are so difficult to treat that 50% of patients infected by them die. In the 2013 Antibiotic Resistance Threat report, the CDC identifies three major concerns: 1) new active molecules are harder to discover and produce, 2) development costs are prohibitive, and 3) resistance spreads faster than ever. The World Health Organization (WHO) warns that "[i]n the absence of urgent corrective and protective actions, the world is heading toward a post-antibiotic era, in which many common infections will no longer have a cure and [will], once again, kill unabated." (World Health Day, Combat Drug Resistance: No Action Today Means No Cure Tomorrow, Statement by WHO Director-General, Dr. Margaret Chan. Apr. 6, 2011, http://www.who.int/mediacentre/news/statements/2011/whd_20110407/en/.) In 2013, the Center for Disease Control (CDC) estimated that 70 percent of the bacteria that caused hospital-acquired infections were resistant to at least one of the relevant antibiotics. (Antibiotic Resistance Threats in the United States, 2013, Centers for Disease Control and Prevention: Atlanta, Ga., http://www.cdc.gov/drugresistance/threat-report-2013/.) It has long been argued by public advocacy groups, such as the Alliance for the Prudent Use of Antibiotics, that antibiotics are societal drugs. Individual use affects the entire community.

Such antibiotic resistance has become a worldwide concern now that the consequences of antibiotic overuse are being studied and reported. The CDC now estimates that in the U.S. at least 23,000 people die from multiple antibiotic-resistant bacteria infections every year. Id. In the U.S. alone, these superbug infections are responsible for $20 billion in excess healthcare costs, $35 billion in societal costs, and 8 million additional hospital stays each year. (Roberts et al., *Clin. Infect. Dis.* 49(8): 1175-84 (2009).)

In agriculture, seeds can spread plant bacterial and fungal diseases across farms, states, and countries. In some instances, seedlings fail due to "damping off." This is the death of a seedling before or shortly after emergence due to decomposition of the root and/or lower stem. Control of such diseases may begin with the seeds. Seed treatments should protect seeds from pathogens such as bacteria, viruses, and fungi. Thus, high-quality, disease-free seeds are an important part of obtaining higher plant yields and food safety.

In agriculture, bacteria can also contaminate animal environments in high density breeding operations. Pathogenic microbes such as *Salmonella* and *Listeria* entering the food chain cost hundreds of millions of dollars in product recalls and hospitalizations. (Hoffmann, S. and T. D. Anekwe, *Making Sense of Recent Cost-of-Foodborne-Illness Estimates*, United States Department of Agriculture, Economic Research Service, 2013, http://www.ers.usda.gov/publications/eib-economic-information-bulletin/eib118.aspx; Hoffmann et al., *J. Food Prot.* 75(7): 1292-1302 (2012).)

Some food borne pathogens are also known to be become antibiotic-resistant. Foodborne pathogens have a vast impact on Americans, causing 48 million illnesses, 28,000 hospitalizations, and at least 3,000 deaths each year. (http://www.cdc.gov/foodborneburden/2011-foodborne-estimates.html.) They also have a tremendous impact on businesses and the healthcare system resulting in annual costs of $14-$16 billion. This includes direct medical costs and value of time lost to illness. Bacteria are the primary culprits. They comprise four of the top five pathogens that contribute to illness, three of the top five that cause hospitalizations, and three of the top five that cause mortality.

Nematodes are microscopic worms that cause eighty billion dollars of crop loss in the world each year. Plant-parasitic nematodes threaten crops throughout the world. In fact, all crops are damaged by at least one species of nematode. They attack almost every part of the plant including roots, stems, leaves, fruits and seeds.

Some 5,000 species of nematodes are estimated to be parasites of vertebrate animals and humans. These species are often characterized in a larger group of worm parasites as helminths. Strategies for managing nematode parasites of domestic vertebrate animals include control of secondary hosts or vectors and the use of chemical anthelminthics. Roundworms can infect dogs, cats, cattle, sheep, pigs, and poultry.

Most parasitic roundworms have direct life cycles, i.e. the free-living stages that do not need an intermediate host for development. They can directly infect their final host where they migrate to their predilection sites and complete development to adults. Inside the final host, pregnant females produce thousands of eggs that are usually excreted with the feces of the host and contaminate pastures, rivers, lakes, etc.

Controlling plant pathogens relies heavily on synthetic chemicals to maintain high product yields. The public has shown increasing concern, however, over the effects that agrochemical residues have on human health and the environment. (Mark et al., *FEMS Microbiol. Ecol.* 56(2): 167-77 (2006); Ritter et al., *J. Tox. Environ. Health* 9(6):441-56 (2006).) Farmers who use synthetic agrochemicals have more neurological problems that include headaches, fatigue, insomnia, dizziness and hand tremors. (http://www.niehs.nih.gov/health/topics/agents/pesticides/). Agrochemicals may also cause birth defects, nerve damage, cancer, decreased sperm motility and acute poisoning (Moses, *AAOHN J.*, 37(3): 115-30 (1989); Reeves and Schafer Int'l J., *Occup. Environ. Health* 9(1):30-39 (2003): Carozza et al., *Environ. Health Perspect.* 116(4):559-65 (2008); U.S. Environmental Protection Agency, 2014, http://www.epa.gov/pesticides/food/risks.htm). Furthermore, protecting crops from fungal pathogens is particularly challenging for organic crops on which synthetic antifungal chemicals cannot be used.

Fungicides and antibiotics are widely used in developed agricultural systems to control disease and safeguard crop yield and quality. Over time, however, resistance to many of the most effective fungicides and antibiotics has emerged and spread in pathogen populations (Lucas et al., Adv Appl Microbiol., 90:29-92 (2015)). The widespread practice of routinely dosing farm animals with antifungals and antibiotics is contributing to this threat. Much of this use is for preventing, rather than treating, disease. Drug-resistant microbes carried by farm animals can spread to humans through consumption of contaminated food, from direct contact with animals, or by environmental spread, for example, in contaminated water or soil. Antibiotic and fungicide resistant pathogens of humans and farm animals are emerging and spreading at a rate that may not be contained by the development of new drugs.

Thus there is a significant need for new methods of controlling fungal, bacterial, oomycete, and nematode pathogens that cause agricultural contamination or infections as well as human infections.

SUMMARY OF THE INVENTION

The present invention provides compositions and methods for reducing microbial contamination or infection in plants, animals, fabrics, and products therefrom. The present invention also provides compositions and methods for reducing human infections. The present invention also reduces the emergence of resistance in microbes towards chemical biocides. In particular, the invention provides magnetic nanoparticles comprising microbiocidal and/or microbiostatic enzymes in one component, substrates for the enzymes in a second component, and a chemical microbiocidal agent that works synergistically with the enzymes. The compositions are dormant and become active upon exposure to hydration, oxygen, or mixing.

Thus, the invention provides a solid fungicidal composition, comprising: a first component having self-assembled mesoporous aggregates of magnetic nanoparticles comprising a hydrogen peroxide producing enzyme and a free radical producing enzyme: a second component having a first substrate for said hydrogen peroxide producing enzyme and a second substrate for said free radical producing enzyme; and a chemical fungicide: wherein said composition is essentially inactive, wherein exposure of said first and second components to hydration or oxygen activates said composition and results in said substrate for said hydrogen peroxide producing enzyme being oxidized into hydrogen peroxide, wherein said hydrogen peroxide acts as a substrate for said free radical producing enzyme, and wherein said free radicals are produced having fungicidal activities.

In some embodiments, said chemical fungicide is selected from the group consisting of mefenoxam, myclobutanil, chlorothalonil, prothioconazole, trifloxystrobin, propiconazole, mancozeb, and copper. In a preferred embodiment, said chemical fungicide is chlorothalonil. In another preferred embodiment, said chemical fungicide is mancozeb.

The invention provides a solid bactericidal composition, comprising; a first component having self-assembled mesoporous aggregates of magnetic nanoparticles comprising a hydrogen peroxide producing enzyme and a free radical producing enzyme; a second component having a first substrate for said hydrogen peroxide producing enzyme and a second substrate for said free radical producing enzyme; and a chemical antibiotic; wherein said composition is essentially inactive, wherein exposure of said first and second components to hydration or oxygen activates said composition and results in said substrate for said hydrogen peroxide producing enzyme being oxidized into hydrogen peroxide, wherein said hydrogen peroxide acts as a substrate for said free radical producing enzyme, and wherein said free radicals are produced having bactericidal activities.

In some embodiments, said chemical antibiotic is selected from the group consisting of ampicillin, streptomycin, vancomycin, and copper.

The invention provides a liquid fungicidal composition, comprising; a first component having self-assembled mesoporous aggregates of magnetic nanoparticles comprising a free radical producing enzyme; a second component having a substrate for said free radical producing enzyme and a hydrogen peroxide source: and a chemical fungicide; wherein said composition is essentially inactive, wherein mixing said first and second components activates said composition and results in said hydrogen peroxide source acting as a substrate for said free radical producing enzyme, and wherein said free radicals are produced having fungicidal activities.

In some embodiments, said chemical fungicide is selected from the group consisting of mefenoxam, myclobutanil, chlorothalonil, prothioconazole, trifloxystrobin, propiconazole, mancozeb, an essential oil, and copper. In a preferred embodiment, said chemical fungicide is chlorothalonil. In another preferred embodiment, said essential oil is tea tree oil (TTO).

The invention provides a liquid bactericidal composition, comprising; a first component having self-assembled mesoporous aggregates of magnetic nanoparticles comprising a free radical producing enzyme; a second component having a substrate for said free radical producing enzyme and a hydrogen peroxide source; and a chemical antibiotic; wherein said composition is essentially inactive, wherein mixing said first and second components activates said composition and results in said hydrogen peroxide source acting as a substrate for said free radical producing enzyme, and wherein said free radicals are produced having bactericidal activities.

In some embodiments, the final chemical fungicide concentration is between about 10% and 2500% of the half maximal effective concentration ($EC_{50}$). In other embodiments, the final chemical antibiotic concentration is between about 1 and 100% of the minimum inhibitory concentration (MIC) or minimum bactericidal concentration (MBC).

In other embodiments of the invention, the compositions and methods disclosed herein comprise microbiocidal compositions that comprise both a chemical antibiotic and a chemical fungicide.

In some embodiments of the invention, said mesoporous aggregates of magnetic nanoparticles have an iron oxide composition. In other embodiments of the invention, said mesoporous aggregates of magnetic nanoparticles have a magnetic nanoparticle size distribution in which at least 90% of magnetic nanoparticles have a size of at least about 3 nm and up to about 30 nm, and an aggregated particle size distribution in which at least about 90% of said mesoporous aggregates of magnetic nanoparticles have a size of at least about 10 nm and up to 500 nm. In other embodiments of the invention, said mesoporous aggregates of magnetic nanoparticles possess a saturated magnetization of at least 10 emu/g.

In some embodiments of the invention, said free-radical-producing enzyme and hydrogen peroxide producing enzyme are contained in said mesoporous aggregates of magnetic nanoparticles in up to about 100% of saturation capacity.

In some embodiments of the invention, said hydrogen peroxide generating enzyme is an oxidase. In other embodiments of the invention, said oxidase is glucose oxidase or alcohol oxidase.

The invention provides an agricultural product comprising the fungicidal and bactericidal compositions disclosed herein. In some embodiments, the invention provides a liquid pesticide product comprising the fungicidal and bactericidal compositions disclosed herein. In other embodiments, the invention provides a seed coating, comprising the fungicidal or bactericidal compositions disclosed herein. In some embodiments, the invention provides a seed comprising the seed coatings disclosed herein, wherein said seed is selected from the group consisting of vegetable, fruit, flower and field crop.

In preferred embodiments, said vegetable seed is selected from the group consisting of tomato, pea, onion, garlic, parsley, oregano, basil, cilantro, carrot, cabbage, corn, cucumber, radish, pepper, broccoli, cauliflower, cucumber, spinach, kale, chard, artichoke, and lettuce. In other preferred embodiments, said fruit seed is selected from the group consisting of citrus, tomato, orange, lemon, lime, avocado, clementine, apple, persimmon, pear, peach, nectarine, berry, strawberry, raspberry, grape, blueberry, blackberry, cherry, apricot, gourds, squash, zucchini, eggplant, pumpkin, coconut, guava, mango, papaya, melon, honeydew, cantaloupe, watermelon, banana, plantain, pineapple, quince, sorbus, loquata, plum, currant, pomegranate, fig, olive, fruit pit, a nut, peanut, almond, cashew, hazelnut, brazil nut, pistachio, and macadamia. In other preferred embodiments, said field crop is selected from the group consisting of corn, wheat, soybean, canola, sorghum, potato, sweet potato, yam, lentils, beans, cassava, coffee, hay, buckwheat, oat, barley, rape, switchgrass, elephant grass, beet, sugarcane, and rice. In other preferred embodiments, said flower seed is selected from the group consisting of annual, perennial, bulb, flowering woody stem, carnation, rose, tulip, poppy, snapdragon, lily, mum, iris, alstroemeria, pom, fuji, and bird of paradise.

The invention provides an animal bedding, comprising the fungicidal or bactericidal compositions disclosed herein.

The invention provides a wound dressing, comprising the fungicidal or bactericidal compositions disclosed herein.

The invention provides a fabric, comprising the fungicidal or bactericidal compositions disclosed herein.

The invention provides a method of improving a plant product yield, comprising exposing the improved seeds disclosed herein to hydration and oxygenation prior to or during the planting or germination of said plant.

The invention provides a method of improving an animal product yield, comprising exposing the improved animal bedding disclosed herein to hydration and oxygen prior to or during use by said animal. In a preferred embodiment, said hydration is from said animal's urine. In other preferred embodiments, said animal product is selected from the group consisting of live animals, milk, meat, fat, eggs, bodily fluids, blood, serum, antibodies, enzymes, rennet, bone, animal byproducts, and animal waste.

In other preferred embodiments, said animal is selected from the group consisting of cows, pigs, chickens, turkeys, horses, sheep, goats, donkeys, mules, ducks, geese, buffalo, camels, yaks, llama, alpacas, mice, rats, dogs, cats, hamsters, guinea pigs, reptiles, amphibians, parrots, parakeets, cockatiels, canaries, pigeons, doves, and insects.

The invention provides a method of reducing sepsis, comprising administering the improved wound dressings disclosed herein to a wound.

The invention provides a method of producing the fungicidal or bactericidal compositions disclosed herein, comprising formulating said first component with a matrix material selected from the group consisting of water-soluble cellulose derivatives, water-solvatable cellulose derivatives, alginate derivatives, and chitosan derivatives and formulating said second component with a matrix material selected from the group consisting of water-soluble cellulose derivatives, water-solvatable cellulose derivatives, alginate derivatives, and chitosan derivatives. In preferred embodiments, said first component is further subjected to spray drying, freeze drying, drum drying, pulse combustion drying, or rotary seed coating. In other preferred embodiments, said second component is further subjected to spray drying, freeze drying, drum drying, pulse combustion drying, or rotary seed coating.

The invention provides a method of reducing or eliminating fungal or bacterial growth, comprising spraying a substance with the liquid fungicidal or bactericidal compositions disclosed herein.

The invention provides a method of protecting an agricultural product from a pathogen, comprising exposing said product to the fungicidal or bactericidal compositions disclosed herein. In preferred embodiments, said pathogen is a plant, animal, or human pathogen. In other preferred embodiments, said pathogen is a fungus, oomycete, or bacterium. In more preferred embodiments, said fungus is selected from the group consisting of *Rhizoctonia* species and *Fusarium* species. In other preferred embodiments, said pathogen is a bacterium selected from the group consisting of *Xanthomonas campestris, Clavibacter michiganensis, Acidovorax avenae, Pseudomonas viridiflava, Pseudomonas syringae, Escherichia coli, Salmonella* species, and *Listeria* species. In other preferred embodiments, said pathogen is an oomycete selected from the group consisting of *Pythium* species and *Phytophthora* species.

The invention provides a method of reducing or eliminating damping off in a plant, comprising exposing said plant to the fungicidal or bactericidal compositions disclosed herein.

The invention provides a solid nematocidal composition, comprising a first component having self-assembled mesoporous aggregates of magnetic nanoparticles comprising a hydrogen peroxide producing enzyme and a free radical producing enzyme and a second component having a first substrate for said hydrogen peroxide producing enzyme and a second substrate for said free radical producing enzyme; wherein said composition is essentially inactive, wherein exposure of said first and second components to hydration or oxygen activates said composition and results in said substrate for said hydrogen peroxide producing enzyme being oxidized into hydrogen peroxide, wherein said hydrogen peroxide acts as a substrate for said free radical producing enzyme, and wherein said free radicals are produced having fungicidal activities.

The invention provides a liquid nematocidal composition, comprising a first component having self-assembled mesoporous aggregates of magnetic nanoparticles comprising a free radical producing enzyme and a second component having a substrate for said free radical producing enzyme and a hydrogen peroxide source; wherein said composition is essentially inactive, wherein mixing said first and second components activates said composition and results in said hydrogen peroxide source acting as a substrate for said free radical producing enzyme, and wherein said free radicals are produced having fungicidal activities.

In a preferred embodiment, the nematocidal compositions further comprising an essential oil. In more preferred embodiments, said essential oil is selected from the group consisting of tea tree (TTO), aegle, *ageratum*, citrus, citronella, orange, pine, *eucalyptus*, marigold, geranium, lemongrass, orange, palmarosa, mint, peppermint, cinnamon, clove, rosemary, thyme, garlic, oregano, anise, cumin, turmeric, *curcuma*, caraway, fennel, onion, and patchouli oil. In a most preferred embodiment, said essential oil is TTO.

The invention provides an agricultural product, comprising the nematocidal compositions described herein. In other embodiments, the invention provides a liquid pesticide product comprising the nematocidal compositions described herein.

The invention provides a seed coating comprising the nematocidal compositions described herein. In some embodiments, said seed is selected from the group consisting of vegetable, fruit, flower and field crop. In preferred embodiments, said vegetable seed is selected from the group consisting of tomato, pea, onion, garlic, parsley, oregano, basil, cilantro, carrot, cabbage, corn, cucumber, radish, pepper, broccoli, cauliflower, cucumber, spinach, kale, chard, artichoke, and lettuce.

In other preferred embodiments, said fruit seed is selected from the group consisting of citrus, tomato, orange, lemon, lime, avocado, clementine, apple, persimmon, pear, peach, nectarine, berry, strawberry, raspberry, grape, blueberry, blackberry, cherry, apricot, gourds, squash, zucchini, eggplant, pumpkin, coconut, guava, mango, papaya, melon, honeydew, cantaloupe, watermelon, banana, plantain, pineapple, quince, sorbus, loquata, plum, currant, pomegranate, fig, olive, fruit pit, a nut, peanut, almond, cashew, hazelnut, brazil nut, pistachio, and macadamia.

In other preferred embodiments, said field crop is selected from the group consisting of corn, wheat, soybean, canola, sorghum, potato, sweet potato, yam, lentils, beans, cassava, coffee, hay, buckwheat, oat, barley, rape, switchgrass, elephant grass, beet, sugarcane, and rice.

In other preferred embodiments, said flower seed is selected from the group consisting of annual, perennial, bulb, flowering woody stem, carnation, rose, tulip, poppy, snapdragon, lily, mum, iris, alstroemeria, pom, fuji, and bird of paradise.

The invention provides an animal bedding, comprising the nematocidal composition described herein.

The invention provides a method of improving a plant product yield, comprising exposing the seed of described herein to hydration and oxygenation prior to or during the planting or germination of said plant.

The invention provides a method of improving an animal product yield, comprising exposing the animal bedding described herein to hydration and oxygen prior to or during use by said animal. In some embodiments, said hydration is from said animal's urine. In other embodiments, said animal product is selected from the group consisting of live animals, milk, meat, fat, eggs, bodily fluids, blood, serum, antibodies, enzymes, rennet, bone, animal byproducts, and animal waste. In other embodiments, said animal is selected from the group consisting of cows, pigs, chickens, turkeys, horses, sheep, goats, donkeys, mules, ducks, geese, buffalo, camels, yaks, llama, alpacas, mice, rats, dogs, cats, hamsters, guinea pigs, reptiles, amphibians, parrots, parakeets, cockatiels, canaries, pigeons, doves, and insects.

The invention provides a method of producing the nematocidal composition described herein, comprising formulating said first component with a matrix material selected from the group consisting of water-soluble cellulose derivatives, water-solvatable cellulose derivatives, alginate derivatives, and chitosan derivatives and formulating said second component with a matrix material selected from the group consisting of water-soluble cellulose derivatives, water-solvatable cellulose derivatives, alginate derivatives, and chitosan derivatives. In some embodiments, said first component is further subjected to spray drying, freeze drying, drum drying, pulse combustion drying, or rotary seed coating. In other embodiments, said second component is further subjected to spray drying, freeze drying, drum drying, pulse combustion drying, or rotary seed coating.

The invention provides a method of reducing or eliminating nematode growth, comprising spraying a substance with the liquid nematocidal compositions described herein.

The invention provides a method of protecting an agricultural product from a nematode, comprising exposing said product to the nematocidal compositions disclosed herein. In some embodiments, said nematode is selected from the group consisting of *Meloidogyne* species (spp.), *Heterodera* spp., *Globodera* spp., *Pratylenchus* spp., *Helicotylenchus* spp., *Radopholus similis, Ditylenchus dipsaci, Rotylenchulus reniformis, Xiphinema* spp, *Aphelenchoides* spp., *Toxocara* spp., *Bursaphelenchus xylophilus*, and *trichinella spiralis*. In preferred embodiments, said nematode is a *Meloidogyne* spp., a *trichinella spiralis*, or a *Toxocara* spp.

BRIEF DESCRIPTION OF THE DRAWINGS

FIG. 1C shows the effect of 1× vs. 10× substrate concentrations averaged across all five LP:GOx enzyme ratios. Each bar represents the mean of ten replicates. Statistical analysis was done using Tukey's Honest Significant Difference (HSD), $P<0.05$).

DETAILED DESCRIPTION OF THE INVENTION

Figure 1A:
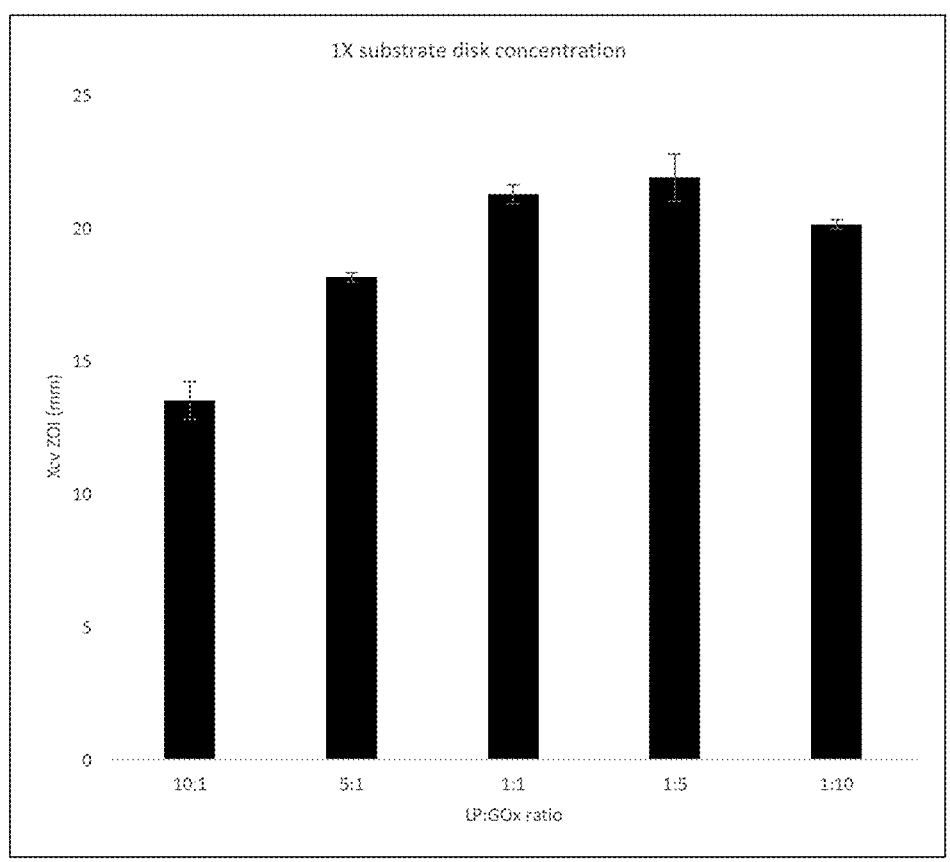
FIGS. 1A, 1B, and 1C. Effect of LP:GOx enzyme ratio and substrate concentration on dry enzyme disk bactericidal efficacy. The analysis was done twice and results were consistent across the two replicates. Data for a single analytical run is shown. The effect of the LP:GOx ratio on zones of inhibition (ZOI) of *Xanthomonas campestris* pv, vitians (Xcv) is shown at 1× (FIG. 1A) and 10× (FIG. 1B) substrate concentrations. Each bar represents the mean of two technical replicates.

The present invention provides compositions and methods for reducing microbial contamination or infection in plants, animals, fabrics, and products therefrom. This is accomplished, for the first time, by the synergy of chemical antimicrobial agents with multicomponent compositions comprising (1) a hydrogen peroxide producing (HPP) enzyme and a free radical producing (FRP) enzyme in self-assembled magnetic nanoparticles in one component and (2) substrates for the enzymes in another component. These magnetically-immobilized enzymes may be in solid or liquid compositions that are stable or inactive. Thus, they may be stored prior to or after incorporation into products. When the fungicidal activities are required, these multicomponent compositions are activated by exposure to hydration and/or oxygen. The HPP enzyme acts on substrates to produce hydrogen peroxide and, e.g. D-glucono-δ-lactone. The FRP enzyme acts on the hydrogen peroxide and one or more further substrates to produce free radicals. The hydrogen peroxide and free radicals have antimicrobial properties. In alternative embodiments, hydrogen peroxide is provided as opposed to a hydrogen peroxide producing enzyme plus its substrates. The antimicrobial activities are activated by exposure to hydration and/or oxygen. The disclosures of Int'l Pub. Nos. WO2012122437 and WO2014055853 as well as Int'l Appl. No. PCT/US16/31419, incorporated by reference herein in their entirety.

Self-assembled mesoporous nanoclusters comprising entrapped peroxidases are highly active and robust. The technology is a powerful blend of biochemistry, nanotechnology, and bioengineering at three integrated levels of organization: Level 1 is the self-assembly of peroxidase and oxidase enzymes with magnetic nanoparticles (MNP) for the synthesis of magnetic mesoporous nanoclusters. This level uses a mechanism of molecular self-entrapment to immobilize and stabilize enzymes. Level 2 is the stabilization of the MNPs into other matrices. Level 3 is product conditioning and packaging for Level 1+2 delivery. The assembly of magnetic nanoparticles adsorbed to enzyme is herein also referred to as a "bionanocatalyst" (BNC).

MNP immobilization provides highly active and cost-effective peroxidases. Peroxidases are very potent enzymes yet notoriously difficult to deploy in industrial settings due to strong inhibition in presence of excess peroxide. NPs increase peroxidation activity and reduce their inhibition which renders them industrially useful. Additionally, the MNPs allow for a broader range of operating conditions such as temperature, ionic strength and pH. The size and magnetization of the MNPs affect the formation and structure of the NPs, all of which have a significant impact on the activity of the entrapped enzymes. By virtue of their surprising resilience under various reaction conditions, MNPs can be used as improved enzymatic or catalytic agents where other such agents are currently used. Furthermore, they can be used in other applications where enzymes have not yet been considered or found applicable.

The BNC contains mesopores that are interstitial spaces between the magnetic nanoparticles. The enzymes are preferably embedded or immobilized within at least a portion of mesopores of the BNC. As used herein, the term "magnetic" encompasses all types of useful magnetic characteristics, including permanent magnetic, superparamagnetic, paramagnetic, ferromagnetic, and ferrimagnetic behaviors.

The magnetic nanoparticle or BNC has a size in the nanoscale, i.e., generally no more than 500 nm. As used herein, the term "size" can refer to a diameter of the magnetic nanoparticle when the magnetic nanoparticle is approximately or substantially spherical. In a case where the magnetic nanoparticle is not approximately or substantially spherical (e.g., substantially ovoid or irregular), the term "size" can refer to either the longest the dimension or an average of the three dimensions of the magnetic nanoparticle. The term "size" may also refer to an average of sizes over a population of magnetic nanoparticles (i.e., "average size").

In different embodiments, the magnetic nanoparticle has a size of precisely, about, up to, or less than, for example, 500 nm, 400 nm, 300 nm, 200 nm, 100 nm, 50 nm, 40 nm, 30 nm, 25 nm, 20 nm, 15 nm, 10 nm, 5 nm, 4 nm, 3 nm, 2 nm, or 1 nm, or a size within a range bounded by any two of the foregoing exemplary sizes.

In the BNC, the individual magnetic nanoparticles can be considered to be primary nanoparticles (i.e., primary crystallites) having any of the sizes provided above. The aggregates of nanoparticles in a BNC are larger in size than the nanoparticles and generally have a size (i.e., secondary size) of at least about 5 nm. In different embodiments, the aggregates have a size of precisely, about, at least, above, up to, or less than, for example, 5 nm, 8 nm, 10 nm, 12 nm, 15 nm, 20 nm, 25 nm, 30 nm, 35 nm, 40 nm, 45 nm, 50 nm, 60 nm, 70 nm, 80 nm, 90 nm, 100 nm, 150 nm, 200 nm, 300 nm, 400 nm, 500 nm, 600 nm, 700 nm, or 800 nm, or a size within a range bounded by any two of the foregoing exemplary sizes.

Typically, the primary and/or aggregated magnetic nanoparticles or BNCs thereof have a distribution of sizes, i.e., they are generally dispersed in size, either narrowly or broadly dispersed. In different embodiments, any range of primary or aggregate sizes can constitute a major or minor proportion of the total range of primary or aggregate sizes. For example, in some embodiments, a particular range of primary particle sizes (for example, at least about 1, 2, 3, 5, or 10 nm and up to about 15, 20, 25, 30, 35, 40, 45, or 50 nm) or a particular range of aggregate particle sizes (for example, at least about 5, 10, 15, or 20 nm and up to about 50, 100, 150, 200, 250, or 300 nm) constitutes at least or above about 50%, 60%, 70%, 80%, 906%, 95%, 98%, 99%, or 100% of the total range of primary particle sizes. In other embodiments, a particular range of primary particle sizes (for example, less than about 1, 2, 3, 5, or 10 nm, or above about 15, 20, 25, 30, 35, 40, 45, or 50 nm) or a particular range of aggregate particle sizes (for example, less than about 20, 10, or 5 nm, or above about 25, 50, 100, 150, 200, 250, or 300 nm) constitutes no more than or less than about 50%, 40%, 30%, 20% 10%, 5%, 2%, 1%, 0.5%, or 0.1% of the total range of primary particle sizes.

The aggregates of magnetic nanoparticles (i.e., "aggregates") or BNCs thereof can have any degree of porosity, including a substantial lack of porosity depending upon the quantity of individual primary crystallites they are made of. In particular embodiments, the aggregates are mesoporous by containing interstitial mesopores (i.e., mesopores located between primar magnetic nanoparticles, formed by packing arrangements). The mesopores are generally at least 2 nm and up to 50 nm in size. In different embodiments, the mesopores can have a pore size of precisely or about, for example, 2, 3, 4, 5, 10, 12, 15, 20, 25, 30, 35, 40, 45, or 50 nm, or a pore size within a range bounded by any two of the foregoing exemplary pore sizes. Similar to the case of particle sizes, the mesopores typically have a distribution of sizes, i.e., they are generally dispersed in size, either narrowly or broadly dispersed. In different embodiments, any range of mesopore sizes can constitute a major or minor proportion of the total range of mesopore sizes or of the total pore volume. For example, in some embodiments, a particular range of mesopore sizes (for example, at least about 2, 3, or 5, and up to 8, 10, 15, 20, 25, or 30 nm) constitutes at least or above about 50%, 60%, 70%, 80%, 90%, 95%, 98%, 99%, or 100% of the total range of mesopore sizes or of the total pore volume. In other embodiments, a particular range of mesopore sizes (for example, less than about 2, 3, 4, or 5 nm, or above about 10, 15, 20, 25, 30, 35, 40, 45, or 50 nm) constitutes no more than or less than about 50%, 40%, 30%, 20%, 10%, 5%, 2%, 1%, 0.5%, or 0.1% of the total range of mesopore sizes or of the total pore volume.

The magnetic nanoparticles can have any of the compositions known in the art. In some embodiments, the magnetic nanoparticles are or include a zerovalent metallic portion that is magnetic. Some examples of such zerovalent metals include cobalt, nickel, and iron, and their mixtures and alloys. In other embodiments, the magnetic nanoparticles are or include an oxide of a magnetic metal, such as an oxide of cobalt, nickel, or iron, or a mixture thereof. In some embodiments, the magnetic nanoparticles possess distinct core and surface portions. For example, the magnetic nanoparticles may have a core portion composed of elemental iron, cobalt, or nickel and a surface portion composed of a passivating layer, such as a metal oxide or a noble metal coating, such as a layer of gold, platinum, palladium, or silver. In other embodiments, metal oxide magnetic nanoparticles or aggregates thereof are coated with a layer of a noble metal coating. The noble metal coating may, for example, reduce the number of charges on the magnetic nanoparticle surface, which may beneficially increase dispersibility in solution and better control the size of the BNCs. The noble metal coating protects the magnetic nanoparticles against oxidation, solubilization by leaching or by chelation when chelating organic acids, such as citrate, malonate, or tartrate, are used in the biochemical reactions or processes. The passivating layer can have any suitable thickness, and particularly, at least, up to, or less than, about for example, 0.1 nm, 0.2 nm, 0.3 nm, 0.4 nm, 0.5 nm, 0.6 nm, 0.7 nm, 0.8 nm, 0.9 nm 1 nm 2 nm 3 nm, 2 nm 34 nm, 5 nm, 6 nm, 7 nm, 8 nm, 9 nm, or 10 nm, or a thickness in a range bounded by any two of these values.

Magnetic materials useful for the invention are well-known in the art. Non-limiting examples comprise ferromagnetic and ferromagnetic materials including ores such as iron ore (magnetite or lodestone), cobalt, and nickel. In other embodiments, rare earth magnets are used. Non-limiting examples include neodymium, gadolinium, sysprosium, samarium-cobalt, neodymium-iron-boron, and the like. In yet further embodiments, the magnets comprise composite materials. Non-limiting examples include ceramic, ferrite, and alnico magnets. In preferred embodiments, the magnetic nanoparticles have an iron oxide composition. The iron oxide composition can be any of the magnetic or superparamagnetic iron oxide compositions known in the art, e.g., magnetite ($FesO/O$, hematite ($\alpha$-$Fe2\theta$ 3), maghemite ($\gamma$-$Fe2C$>3), or a spinel ferrite according to the formula $AB_2O_4$, wherein A is a divalent metal (e.g., $Xn^{2+}$, $Ni^{2+}$, $Mn^{2+}$, $Co^{2+}$, $Ba^{2+}$, $Sr^{2+}$, or combination thereof) and B is a trivalent metal (e.g., $Fe^{3+}$, $Cr^{3+}$, or combination thereof).

The individual magnetic nanoparticles or aggregates thereof or BNCs thereof possess any suitable degree of magnetism. For example, the magnetic nanoparticles, BNCs, or BNC scaffold assemblies can possess a saturated magnetization (Ms) of at least or up to about 5, 10, 15, 20, 25, 30, 40, 45, 50, 60, 70, 80, 90, or 100 emu/g. The magnetic nanoparticles, BNCs, or BNC-scaffold assemblies preferably possess a remnant magnetization (Mr) of no more than (i.e., up to) or less than 5 emu/g, and more preferably, up to or less than 4 emu/g, 3 emu/g, 2 emu/g, 1 emu/g, 0.5 emu/g, or 0.1 emu/g. The surface magnetic field of the magnetic nanoparticles, BNCs, or BNC-scaffold assemblies can be about or at least, for example, about 0.5, 1, 5, 10, 50, 100, 200, 300, 400, 500, 600, 700, 800, 900, or 1000 Gauss (G), or a magnetic field within a range bounded by any two of the foregoing values. If microparticles are included, the microparticles may also possess any of the above magnetic strengths.

The magnetic nanoparticles or aggregates thereof can be made to adsorb a suitable amount of enzyme, up to or below a saturation level, depending on the application, to produce the resulting BNC. In different embodiments, the magnetic nanoparticles or aggregates thereof may adsorb about, at least, up to, or less than, for example, 1, 5, 10, 15, 20, 25, or 30 pmol/m2 of enzyme. Alternatively, the magnetic nanoparticles or aggregates thereof may adsorb an amount of enzyme that is about, at least, up to, or less than, for example, about 10%, 20%, 30%, 40%, 50%, 60%, 70%, 80%, 90%, or 100% of a saturation level.

The magnetic nanoparticles or aggregates thereof or BNCs thereof possess any suitable pore volume. For example, the magnetic nanoparticles or aggregates thereof can possess a pore volume of about, at least, up to, or less than, for example, about 0.01, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1 cm3/g, or a pore volume within a range bounded by any two of the foregoing values. [0052] The magnetic nanoparticles or aggregates thereof or BNCs thereof possess any suitable specific surface area. For example, the magnetic nanoparticles or aggregates thereof can have a specific surface area of about, at least, up to, or less than, for example, about 50, 60, 70, 80, 90, 100, 110, 120, 130, 140, 150, 160, 170, 180, 190, or 200 m 2/g.

MNPs, their structures, organizations, suitable enzymes, and uses are described in WO2012122437 and WO2014055853, incorporated by reference herein in their entirety.

The compositions and methods of the invention, among other things, reduce or eliminate plant death due to pathogens. In some embodiments, the invention reduces or eliminates "damping off." The American Phytopathological Society defines damping-off as "the death of a seedling before or shortly after emergence due to decomposition of the root and/or lower stem; it is common to distinguish between pre-emergence damping-off and post-emergence damping-off. Pre-emergence damping-off occurs before a seedling emerges from the soil line. Post-emergence damping-off occurs shortly after a seedling emerges from the soil line. The disease is commonly caused by the fungus *Rhizoconia solani* and numerous species in the oomycete genus *Pythium*, although other fungi and oomycetes can contribute. The disease is not crop-specific and causes losses to all agricultural crops.

In other embodiments, the assemblies have antimicrobial properties against a wide array of pathogens. In some embodiments, the pathogens include pathogenic plant bacteria species such as *Acidovorax avenae, Agrobacterium tumefaciens, Burkholderia andropogonis, Burkholderia caryophylli, Burkholderia glumae, Candidatus Liberibacter, Candidatus Phytoplasma solani, Clavibacter michiganensis, Dickeya dadantti, Erwinia psidii, Pectobacterium atrosepticum, Pectobacterium betavasculorum, Pectobacterium carotovorum, Pectobacterium carotovorum* subsp. *betavasculorum, Pectobacterium wasabiae, Phytoplasma, Pseudomonas amygdali, Pseudomonas asplenii, Pseudomonas caricapapayae, Pseudomonas cichorii, Pseudomonas coronafaciens, Pseudomonas corrugate, Pseudomonas ficuserectae, Pseudomonas flavescens, Pseudomonas fuscovaginae, Pseudomonas helianthi, Pseudomonas marginalis, Pseudomonas oryzihabitans, Pseudomonas palleroniana, Pseudomonas papaveris, Pseudomonas salomonii, Pseudomonas savastanoi, Pseudomonas syringae, Pseudomonas tomato, Pseudomonas turbinellae, Pseudomonas viridiflava, Psyllid yellows, Ralstonia solanacearum, Rhodococcus fascians, Spiroplasma citri, Xanthomonas* axonopodis, *Xanthomonas campestris, Xanthomonas oryzae, Xylella fastidiosa, Escherichia coli, Salmonella enterica, Listeria monocytogenes*, and other plant, animal, human, soilborne, and environmental pathogens.

In other embodiments, the assemblies have antimicrobial properties against non-plant pathogen bacteria including *Escherishia Coli, Brucella* sp., *Vibrio* sp., *Serrati* asp., *Nocardia* sp., *Leptospira* sp., *Mycobacterium* sp., *Clostridium* sp., *Bacillus* sp., *Pseudomonas* sp. *Staphylococcus* sp., *Neisseria* sp., *Haemophilus* sp., *Helicobacter* sp., *Mycoplasma* sp., *Pseudomonas* sp. *Treponema* sp., and *Yersinia* sp.

In other embodiments, the fungicidal assemblies are effective against plant pathogenic fungi including genera such as *Alternaria* sp., *Armillaria* sp. *Ascochyta* sp., *Aspergillus* sp., *Bipoloaris, Bjerkandera* sp., *Botrytis* sp., *Ceratobasidium* sp., *Cercospora* sp., *Chrysimyxa* sp., *Cladosporium* sp., *Cochliobolus* sp., *Coleosporium* sp., *Colletotrichum* sp., *Cylindrocladium* sp., *Cytospora* sp., *Diaporthe* sp., *Didymella* sp., *Drechslera* sp., *Erysiphe* sp, *Exobasidium* sp., *Fusarium* sp., *Ganoderma* sp., *Gibberella* sp., *Gymnospragium* sp., *Helicobasidium* sp., *Inonotus* sp., *Leptosphaeria* sp., *Leucostoma* sp. *Marasmius* sp., *Microspaera* sp., *Mucor* sp., *Mycosphaerella* sp., *Nectria* sp., *Oidium* sp., *Passalora* sp., *Pestalotiopsis* sp., *Phaeoramularia* sp., *Phoma* sp., *Phyllosticta* sp., *Pseudocercospora* sp., *Puccinia* sp., *Pyrenophora* sp., *Rhizoctonia* sp., *Rhizopus* sp., *Septoria* sp., *Sphaceloma* sp., *Stemphylium* sp., *Stigmina* sp., *Tilletia* sp., *Typhula* sp., *Uromyces* sp., *Ustilago* sp., and *Verticillium* sp.

In other embodiments, the fungicidal assemblies are effective against plant pathogenic oomycetes including genera such as *Aphanomyces* sp., *Bremia* sp., *Peronosclerospora* sp., *Peronospora* sp., *Phytophthora* sp., *Plasmopara* sp., *Pseudoperonospora* sp., *Pythium* sp, and *Sclerophthora* sp. In preferred embodiments, the oomycetes are *Phytophthora infestans, Hyaloperonospora arabidopsidis, Phytophthora ramorum, Phytophthora sojae, Phytophthora capsici, Plasmopara viticola, Phytophthora cinnamomi, Phytophthora parasitica, Pythium ultimum,* or *Albugo candida*.

A number of genera and species of nematodes are highly damaging to a great range of plants, including foliage plants, agronomic and vegetable crops, fruit and nut trees, turfgrass, and forest trees. Thus, in some embodiments, the assemblies of the invention are effective against nematodes such as *Meloidogyne* species (spp.), *Heterodera* spp., *Globodera* spp., *Pralylenchus* spp., *Helicotylenchus* spp., *Radopholus similis, Ditylenchus dipsaci, Rotylenchulus reniformis, Xiphunema* spp, *Aphelenchoides* spp., *Toxocara* spp., *Bursaphelenchus xylophilus*, and *trichinella spiralis*.

In other embodiments, the invention is effective against plant viruses that include plant viruses such as Mosaic Viruses, Mottle Viruses, Begomoviruses, Carlaviruses, Carmoviruses, Criniviruses, Fabaviruses, Furoviruses, Machlomoviruses, Macluraviruses, Necroviruses, Potexviruses, Tenuiviruses, and Tospoviruses.

In some embodiments, the invention provides hydrogen peroxide producing (HPP) enzymes. In certain embodiments, the HPP enzymes are oxidases that may be of the EX 1.1.3 subgenus. In particular embodiments, the oxidase may be EC 1.1.3.3 (malate oxidase), EC 1.1.3.4 (glucose oxidase), EC 1.1.3.5 (hexose oxidase), EC 1.1.3.6 (cholesterol oxidase), EC 1.1.3.7 (aryl-alcohol oxidase), EC 1.1.3.8 (L-gulonolactone oxidase), EC 1.1.3.9 (galactose oxidase), EC 1.1.3.10 (pyranose oxidase), EC 1.1.3.11 (L-sorbose oxidase), EC 1.1.3.12 (pyridoxine 4-oxidase), EC 1.1.3.13 (alcohol oxidase), EC 1.1.3.14 (catechol oxidase), EC 1.1.3.15 (2-hydroxy acid oxidase), EC 1.1.3.16 (ecdysone oxidase), EC 1.1.3.17 (choline oxidase), EC 1.1.3.18 (secondary-alcohol oxidase), EC 1.1.3.19 (4-hydroxymandelate oxidase), EC 1.1.3.20 (long-chain alcohol oxidase), EC 1.1.3.21 (glycerol-3-phosphate oxidase), EC 1.1.3.22, EC 1.1.3.23 (thiamine oxidase), EC 1.1.3.24 (L-galactonolactone oxidase), EC 1.1.3.25, EC 1.1.3.26, EC 1.1.3.27 (hydroxyphytanate oxidase), EC 1.1.3.28 (nucleoside oxidase), EC 1.1.3.29 (Nacylhexosamine oxidase), EC 1.1.3.30 (polyvinyl alcohol oxidase), EC 1.1.3.31, EC 1.1.3.32, EC 1.1.3.33, EC 1.1.3.34, EC 1.1.3.35, EC 1.1.3.36, EC 1.1.3.37 D-arabinono-1,4-lactone oxidase), EC 1.1.3.38 (vanillyl alcohol oxidase), EC 1.1.3.39 (nucleoside oxidase, $H_2O_2$ forming), EC 1.1.3.40 (D-mannitol oxidase), or EC 1.1.3.41 (xylitol oxidase).

The invention provides Free Radical Producing (FRP) enzymes in one of the sequential components of the solid fungicidal compositions. In some embodiments, the FRP is a peroxidase. Peroxidases are widely found in biological systems and form a subset of oxidoreductases that reduce hydrogen peroxide ($H_2O_2$) to water in order to oxidize a large variety of aromatic compounds ranging from phenol to aromatic amines.

Peroxidases belong to the sub-genus EC 1.11.1. In certain embodiments, the EC 1.11.1 enzyme is The EC 1.11.1 enzyme can be more specifically, for example, EC 1.11.1.1 (NADH peroxidase), EC 1.11.1.2 (NADPH peroxidase), EC 1.11.1.3 (fatty acid peroxidase), EC 1.11.1.4, EC 1.11.1.5 (cytochrome-c peroxidase), EC 1.11.1.6 (catalase), EC 1.11.1.7 (peroxidase), EC 1.11.1.8 (iodide peroxidase), EC 1.11.1.9 (glutathione peroxidase), EC 1.11.1.10 (chloride peroxidase), EC 1.11.1.11 (L-ascorbate peroxidase), EC 1.11.1.12 (phospholipid-hydroperoxide glutathione peroxidase), EC 1.11.1.13 (manganese peroxidase), EC 1.11.1.14 (diarylpropane peroxidase), or EC 1.11.1.15 (peroxiredoxin).

In other embodiments, the peroxidase may also be further specified by function, e.g., a lignin peroxidase, manganese peroxidase, or versatile peroxidase. The peroxidase may also be specified as a fungal, microbial, animal, or plant peroxidase. The peroxidase may also be specified as a class I, class II, or class III peroxidase. The peroxidase may also be specified as a myeloperoxidase (MPO), eosinophil peroxidase (EPO), lactoperoxidase (LPO), thyroid peroxidase (TPO), prostaglandin H synthase (PGHS), glutathione peroxidase, haloperoxidase, catalase, cytochrome c peroxidase, horseradish peroxidase, peanut peroxidase, soybean peroxidase, turnip peroxidase, tobacco peroxidase, tomato peroxidase, barley peroxidase, or peroxidasin. In these particular embodiments, the peroxidase is a lactoperoxidase.

The lactoperoxidase/glucose oxidase (LP/GOX) antimicrobial system occurs naturally in bodily fluids such as milk, saliva, tears, and mucous (Bosch et al., *J. Applied Microbiol.*, 89(2), 215-24 (2000)). This system utilizes thiocyanate (SCN−) and iodide (I−), two naturally occurring compounds that are harmless to mammals and higher organisms (Welk et al. *Archives of Oral Biology*, 2587 (2011)). LP catalyzes the oxidation of thiocyanate and iodide ions into hypothiocyanite (OSCN−) and hypoiodite (OI−), respectively, in the presence of hydrogen peroxide ($H_2O_2$). The $H_2O_2$ in this system is provided by the activity of GOX on β-D-glucose in the presence of oxygen. These free radical compounds, in turn, oxidize sulfhydryl groups in the cell membranes of microbes (Purdy, Tenovuo et al. *Infection and Immunity*, 39(3), 1187 (1983); Bosch et al., *J. Applied Microbiol.*, 89(2), 215-24 (2000), leading to impairment of membrane permeability (Wan, Wang et al. *Biochemistry Journal*, 362, 355-362 (2001)) and ultimately microbial cell death. Concentrations as low as 20 µM of hypothiocyanite and hypoiodite can result in inhibition of cell growth (Bosch, van Doorne et al. 2000). The LP/GOX system is effective on thiocyanate on its own: when paired with iodide, there is a synergistic effect that enhances biostatic and biocidal activity and extends the susceptible target range including Gram negative bacteria (e.g., *E. coli, P. aerugenosa*), Gram positive bacteria (e.g., *S. aureus, Streptococcus* spp.), and fungus (e.g., *C. albicans*) (Reiter, Marshall et al. *Infection and Immunity*, 13(3), 800-807 (1976); Bosch et al., *J. Applied Microbiol.*, 89(2), 215-24 (2000); Welk et al. *Archives of Oral Biology*, 2587 (2011).) Furthermore, the LP/GOX system functions in two phases: (1) the generation and action of hypothiocyanite and hypoiodite on cell membranes, and then, when these compounds are depleted, (2) excess $H_2O_2$ builds up, enacting its own oxidative damage on cellular structures (Reiter, Marshall et al. 1976). The forgoing references are incorporated herein by reference in their entirety.

The enzyme system has been deployed and approved in the industry for biofilm control such as toothpaste and milk anti-spoiling agents. The system is largely non-specific and robust with few reaction requirements. One study found persistent biostatic and biocidal activity against Gram (−) and (+) bacteria and *C. albicans* after 18 months of re-inoculation every two months Bosch et al. *J. Applied Microbiol.*, 89(2), 215-24 (2000). The effective pH range is 3-7 with a peak LP activity at pH 5 (Reiter, Marshall et al. 1976; Purdy, Tenovuo et al. 1983). Higher activity is typically witnessed against bacteria at pH 3, but this is likely due to inhibition of growth by low pH (Reiter, Marshall et al. 1976). Other than pH, the only strict requirement for activity of the LP/GOX system is the presence of oxygen, without which GOX can't generate $H_2O_2$ from glucose. The forgoing references are incorporated herein by reference in their entirety.

LP/GOX has been described as a pesticide for microorganisms that include bacteria and fungi. (See U.S. Pat. No. 6,447,811, incorporated by reference herein in its entirety). Thus, in some embodiments, the invention described herein provides magnetically-immobilized pesticides in solid or liquid formulations. The pesticides comprise a peroxidase enzyme that produces a free radical. In some embodiments, the peroxidase enzyme is lactoperoxidase. The pesticides further comprise a peroxide source that may include an enzyme that oxidizes glucose.

In some embodiments of the invention, the chemical fungicide may be one or more of the following: mefenoxam, myclobutanil, chlorothalonil, prothioconazole, trifloxystrobin, propiconazole, mancozeb, Copper, methyl benzimidazole carbamates, dicarboximides, demethylation inhibitors (DMI), phenylamides (PA), amines, phosphorothiolates, dithiolanes, carboxamides, hydroxy-(2-amino-) pyrimidines, anilino-pyrimidines (AP), N-phenyl carbamates, quinone outside inhibitors (QOI), phenylpyrroles (PP), quinolines, aromatic hydrocarbons (AH), heteroaromatics, melanin biosynthesis inhibitors—dehydratase (MBI-D), hydroxyanilides, succinate biosynthesis inhibitors (SBI), polyoxins, phenylureas, quinone inside inhibitors (QiI), benzamides, enopyranuronic acid antibiotic, hexopyranosyl antibiotic, glucopyranosyl antibiotic, cyanoacetamide-oximes, carbamates, uncouplers of oxidative phosphorylation, organo tin compounds, carboxylic acids, heteroaromatics, phosphonates, phthalamic acids, benzotriazines, benzenesulfonomides, pyridazinones, ATP production inhibitors, complex I of respiration inhibitors, carboxylix acid amides (CAA), tetracycline antibiotic, thiocarbamate, host plant defense inducers including salicylic acid pathway, fungicides with unknown target sites of action, fungicides with multi-site contact activity, mineral oils, organic oils, or potassium bicarbonate.

In some embodiments of the invention, a chemical antibiotic is used that may be one or more of the following: chemical families of aminoglycosides, ansamycins, carbacephems, carbapenems, cephalosporins, glycopeptides, lincosamides, lipopeptides, macrolides, monolactams, nitrofurans, oxazolidinones, penicillins, polypeptide antibiotics, quinolones, fluoroquinolones, sulfonamides, tetracyclines, aminoglycosides, ansamycins, carbapenems, cephalosporins, glycopeptides, lincosamides, lipopeptides, macrolides, monobactams, nitrofurans, oxazolidinones, penicillins, polypeptides, quinolones, rifamycins, streptogramins, sulfonamides, tetracyclines, tuberactinomycins, or drugs with activity against mycobacteria. In preferred embodiments, the chemical antibiotic is ampicillin.

The invention provides that the chemical fungicides and antibiotics (chemical microbiocides) may be measured by its minimum inhibitory concentration (MIC) in the compositions and methods described herein. The MIC is the lowest concentration of a chemical that prevents visible growth of a bacterium, fungus, or oomycete. The MIC of the microbiocides may be determined, for instance, by preparing solutions of the chemical at increasing concentrations, incubating the solutions with the separate batches of cultured bacteria, and measuring the results using agar dilution or broth microdilution The minimum bactericidal concentration (MBC) is the lowest concentration of an antibacterial agent required to kill a particular bacterium. It can be determined from broth dilution minimum inhibitory concentration (MIC) tests by subculturing on agar plates that do not contain the test agent. The MBC is identified by determining the lowest concentration of antibacterial agent that reduces the viability of the initial bacterial inoculum by ≥99.9%. The MBC is complementary to the MIC; whereas the MIC test demonstrates the lowest level of antimicrobial agent that inhibits growth, the MBC demonstrates the lowest level of antimicrobial agent that results in microbial death. This means that even if a particular MIC shows inhibition, plating the bacteria onto agar might still result in organism proliferation because the antimicrobial did not cause death. Antibacterial agents are usually regarded as bactericidal if the MBC is no more than four times the MIC. Microorganisms may survive microbiocides because they develop resistance to them.

The final chemical fungicide or antibiotic in the invention is at a final concentration of less than 1% or about 1%, 2%, 3%, 4%, 5%, 6%, 7%, 8%, 9% 10%, 20%, 30%, 40%, 50%, 60%, 70%, 80%, 90%, 100% of the minimum inhibitory concentration (MIC) or minimum bactericidal concentration (MBC).

The chemical microbiocides in the invention can also be measured by their $EC_{50}$. The term half maximal effective concentration ($EC_{50}$) refers to the concentration of a drug, antibody or toxicant which induces a response halfway between the baseline and maximum after a specified exposure time. It is used herein as a measure of microbiocide potency. The $EC_{50}$ of a graded dose response curve therefore represents the concentration of a compound where 50% of its maximal effect is observed. The EC50 of a quantal dose response curve represents the concentration of a compound where 50% of the population exhibit a response after a specified exposure duration. The microbiocides in the invention, including the fungicides and antibiotics, is at a final concentration of less than 1% or about 1%, 2%, 3%, 4%, 5%, 6%, 7%, 8%, 9% 10%, 20%, 30%, 40%, 50%, 60%, 70%, 80%, 90%, 100%. In other embodiments, the final chemical microbiocidal concentration is between about 100% and 500%, 500% and 1000%, 1000% and 2000%, 2000% and 2500%, 2500% and 5000%, 5000% and 10,000%.

The invention provides inactive magnetically-immobilized enzymes. The enzymes may be inactive because they are not exposed to water, oxygen, substrates, or any combination thereof. In a preferred embodiment of the present invention, the magnetically-immobilized enzymes are in an oil base. This limits enzymatic activity prior to use. Activation of the immobilized enzymes occurs upon exposure to hydration and/or oxygen. In a more preferred embodiment, the magnetically-immobilized enzymes are in an oil base comprising an agent for emulsifying the oil in an aqueous solution to form an oil-in-water emulsion. In another more preferred embodiment, the oil is a mineral oil, vegetable oil, or animal oil. Exemplary mineral oils include paraffin oil and kerosene-type oils. Exemplary animal oils include fish oils such as herring and mackerel oil. Examples of vegetable oils are peanut oil, sesame oil, rape-seed oil, linseed oil, castor oil, soybean oil, corn germ oil, and cotton-seed oil.

In other embodiments, in order to further facilitate the distribution of the magnetically-immobilized enzymes over a surface, one or more spreading agents known in the art can further be added to the composition or the oil base. In some embodiments, the spreading agents are non-ionogenic surface tension-reducing substances. In preferred embodiments, the spreading agents are ethoxylated alcohols and phosphatidyl lipids.

In other embodiments, one or more adhesives can be added. Adhesives may help prevent the magnetically-immobilized enzymes from being rinsed off the plant by rain or other conditions. Adhesives are well known in the art. Examples are starch, gums such as xanthan gum, gum Arabic and carboxymethyl celluloses (CMCs).

The composition can be applied by means of coating, spraying, sprinkling, atomizing, overhead spraying, watering, immersing, and drip irrigation. A particularly advantageous method for applying the composition is spraying both by means of low volume methods (mist systems) and high volume methods. Drip irrigation can be used for culture systems on rockwool and other growth substrates. The magnetically-immobilized enzymes according to the invention can also be used to disinfect drip irrigation systems. In both latter cases the presence of the oil base is not strictly necessary for an optimal activity. Immersion in a bath with the composition is particularly suitable for the treatment of plant parts, in particular harvestable parts, such as bulbs, tubers, fruits and the like.

The magnetically-immobilized enzymes can be made commercially available in different forms. In a preferred embodiment, the peroxidase activity is delayed as long as possible because this increases the shelf-life of the product. The enzymatic activity starts upon exposure to both hydration (i.e. water) and oxygen. In the present case the glucose oxidaseglucose system is the hydrogen peroxide donor. In more preferred embodiments, the hydrogen peroxide donor is provided separately from the peroxidase. In addition, the oil base and the spreading agent can, if desired, also be packaged separately.

In another embodiment, a kit is provided for forming the composition the kit comprises an optionally concentrated enzyme composition comprising a peroxidase (e.g. lactoperoxidase) and a hydrogen peroxide donor (e.g. glucose oxidase and glucose). In preferred embodiments, the kit may further comprise thiocyanate, iodide, oil, an emulsifier, or spreading agents. In more preferred embodiments, the ingredients are mixed with each other before use. In another embodiment, the kit may comprise one or more ingredients in a concentrated form for dilution or hydration prior to or concurrently with use.

In embodiments where β-D-Glucose is oxidized to $H_2O_2$, or where cellulose derived sugars are oxidized to $H_2O_2$, cellulase enzymes may be provided with the compositions of the invention. In some embodiments, the seed coating further comprises the cellulase.

In some embodiments, the cellulases are exocellulases, endocellulases, hemicellulases, or combinations thereof known in the art. Endocellulase (EC 3.2.1.4) randomly cleaves internal bonds at amorphous sites that create new chain ends. Exocellulase (EC 3.2.1.91) cleaves two to four units from the ends of the exposed chains produced by endocellulase, resulting in the tetrasaccharides or disaccharides, such as cellobiose. There are two main types of exocellulases [or cellobiohydrolases (CBH)]-CBHI works processively from the reducing end, and CBHII works processively from the nonreducing end of cellulose. Cellobiase (EC 3.2.1.21) or beta-glucosidase hydrolyses the exocellulase product into individual monosaccharides. Oxidative cellulases depolymerize cellulose by radical reactions, as for instance cellobiose dehydrogenase (acceptor). Cellulose phosphorylases depolymerize cellulose using phosphates instead of water.

In other embodiments, endocellulases may include EC 3.2.1.4, endo-1,4-beta-D-glucanase, beta-1,4-glucanase, beta-1,4-endoglucan hydrolase, celluase A, cellulosin AP, endoglucanase D, alkali cellulase, cellulase A 3, celludextrinase, 9.5 cellulase, avicelase, pancellase SS, and 1,4-(1,3, 1,4)-beta-D-glucan 4-glucanohydrolase). Cellulases enzymes are typically produced by fungi, bacteria, and protozoans of cellulose). Other names for 'endoglucanases' are: endo-1,4-beta-glucanase, carboxymethyl cellulase (CMCase), endo-1,4-beta-D-glucanase, beta-1,4-glucanase, beta-1,4-endoglucan hydrolase, and celludextrinase.

In some embodiments, the methods described herein use recombinant cells that express the enzymes used in the invention. Recombinant DNA technology is known in the art. In some embodiments, cells are transformed with expression vectors such as plasmids that express the enzymes. In other embodiments, the vectors have one or more genetic signals, e.g., for transcriptional initiation, transcriptional termination, translational initiation and translational termination. Here, nucleic acids encoding the enzymes may be cloned in a vector so that it is expressed when properly transformed into a suitable host organism. Suitable host cells may be derived from bacteria, fungi, plants, or animals as is well-known in the art.

In some embodiments, the invention provides that the matrix material is a biopolymer. Examples include the polysaccharides (e.g., cellulose, hemicellulose, xylan, chitosan, inulin, dextran, agarose, and alginic acid), polylactic acid, and polyglycolic acid. In other embodiments, the matrix material is a water-soluble cellulose derivative, a water-solvatable cellulose derivative, an alginate derivative, and a chitosan derivative.

In some embodiments, the matrix comprises cellulose. Cellulose is an organic compound with the formula $(C_6H_{10}O_5)n$, a polysaccharide consisting of a linear chain of several hundred to many thousands of β(1→4) linked D-glucose units. The cellulose used in the invention may be obtained or derived from plant, algal, or microbial sources. In some embodiments, the invention provides cellulose derivatives known in the art. The hydroxyl groups (—OH) of cellulose can be partially or fully reacted with reagents known in the art. In preferred embodiments, the cellulose derivatives are cellulose esters and cellulose ethers (—OR). In more preferred embodiments, the cellulose derivatives are cellulose acetate, cellulose triacetate, cellulose proprionate, cellulose acetate proprionate (CAP), cellulose acetate butyrate (CAB), nitrocellulose (cellulose nitrate), cellulose sulfate, methylcellulose, ethylcellulose, ethyl methyl cellulose, hydroxyethyl cellulose, hydroxypropyl cellulose (HPC), hydroxyethyl methyl cellulose, hydroxypropyl methyl cellulose (HPMC), ethyl hydroxyethyl cellulose, and carboxymethyl cellulose (CMC).

In some embodiments, the matrix comprises carboxymethyl cellulose. Carboxymethyl cellulose (CMC) or cellulose gum[1] is a cellulose derivative with carboxymethyl groups (—CH2—COOH) bound to some of the hydroxyl groups of the glucopyranose monomers that make up the cellulose backbone. It is synthesized using techniques known in the art, e.g., by the alkali-catalyzed reaction of cellulose with chloroacetic acid. The polar (organic acid) carboxyl groups render the cellulose soluble and chemically reactive. The functional properties of CMC depend on the degree of substitution of the cellulose structure (i.e., how many of the hydroxyl groups have taken part in the substitution reaction), as well as the chain length of the cellulose backbone structure and the degree of clustering of the carboxymethyl substituents.

In some embodiments, the matrix comprises hydroxypropyl cellulose (HPC). HPC is a derivative of cellulose with both water solubility and organic solubility. HPC is an ether of cellulose in which some of the hydroxyl groups in the repeating glucose units have been hydroxypropylated forming —OCH2CH(OH)CH3 groups using propylene oxide. The average number of substituted hydroxyl groups per glucose unit is referred to as the degree of substitution (DS). Complete substitution would provide a DS of 3. Because the hydroxypropyl group added contains a hydroxyl group, this can also be etherified during preparation of HPC. When this occurs, the number of moles of hydroxypropyl groups per glucose ring, moles of substitution (MS), can be higher than 3. Because cellulose is very crystalline, HPC must have an MS about 4 in order to reach a good solubility in water. HPC has a combination of hydrophobic and hydrophilic groups, so it has a lower critical solution temperature (LCST) at 45° C. At temperatures below the LCST, HPC is readily soluble in water; above the LCST, HPC is not soluble. HPC forms liquid crystals and many mesophases according to its concentration in water. Such mesophases include isotropic, anisotropic, nematic and cholesteric. The last one gives many colors such as violet, green and red.

In some embodiments, the matrix comprises methyl cellulose. Methyl cellulose (or methylcellulose) is derived from cellulose. It is a hydrophilic white powder in pure form and dissolves in cold (but not in hot) water, forming a clear viscous solution or gel. Methyl cellulose does not occur naturally and is synthetically produced by heating cellulose with caustic solution (e.g. a solution of sodium hydroxide) and treating it with methyl chloride. In the substitution reaction that follows, the hydroxyl residues (—OH functional groups) are replaced by methoxide (—OCH$_3$ groups).

Different kinds of methyl cellulose can be prepared depending on the number of hydroxyl groups substituted. Cellulose is a polymer consisting of numerous linked glucose molecules, each of which exposes three hydroxyl groups. The Degree of Substitution (DS) of a given form of methyl cellulose is defined as the average number of substituted hydroxyl groups per glucose. The theoretical maximum is thus a DS of 3.0, however more typical values are 1.3-2.6.

In some embodiments, the matrix comprises alginate. Alginate, also called Alginic acid, and algin, is an anionic polysaccharide distributed widely in the cell walls of brown algae. When bound with water it forms a viscous gum. In extracted form it absorbs water quickly; it is capable of absorbing 200-300 times its own weight in water. It is sold in filamentous, granular or powdered forms. The invention provides matrix materials of known alginate and alginate-derived materials. In preferred embodiments, the alginate-derived materials include alginate-polylysine-alginate (APA), Alginate/Poly-1-lysine/Pectin/Poly-1-lysine/Alginate (APPPA), Alginate/Poly-1-lysine/Pectin/Poly-1-lysine/Pectin (APPPP), and Alginate/Poly-L-lysine/Chitosan/Poly-1-lysine/Alginate(APCPA), alginate-polymethylene-co-guanidine-alginate (A-PMCG-A), hydroxymethylacrylate-methyl methacrylate (HEMA-MMA), multilayered HEMA-MMA-MAA, polyacrylonitrile-vinylchloride (PAN-PVC).

In some embodiments, the matrix comprises chitosan. Chitosan is a linear polysaccharide composed of randomly distributed β-(1→4)-linked D-glucosamine (deacetylated unit) and N-acetyl-D-glucosamine (acetylated unit). The amino group in chitosan has a pKa value of ~6.5, which leads to a protonation in acidic to neutral solution with a charge density dependent on pH and the % DA-value. This makes chitosan water soluble and a bioadhesive which readily binds to negatively charged surfaces such as mucosal membranes. It is produced commercially by deacetylating chitin, which is the structural element in the exoskeleton of crustaceans (such as crabs and shrimp) and cell walls of fungi, with sodium hydroxide. Chitosan is used in agriculture as a seed treatment and biopesticide. In winemaking, it is used as a fining agent, also helping to prevent spoilage. It is also used in bandages to reduce bleeding and as an antibacterial agent. It is also be used to help deliver drugs through the skin.

In other embodiments, the matrix materials may be acrylonitrile/sodium methallylsuflonate, (AN-69), polyethylene glycol/poly pentamethylcyclopentasiloxane/polydimethylsiloxane (PEG/PD5/PDMS), poly JVjiV-dimethyl acrylamide (PDMAAm), siliceous encapsulates, and cellulose sulphate/sodium alginate/polymethylene-co-guanidine (CS/A/PMCG).

In some embodiments, the invention provides antimicrobial compositions that are used, inter alia, for seed coatings. Any seeds that are vulnerable to pathogens that respond to the enzyme systems disclosed herein would benefit. In some embodiments, the seeds may be for vegetables, fruits, field crops, and flowers. In other embodiments, the invention provides antimicrobial compositions that are used, inter alia, for bedding for industrially or commercially relevant domesticated animals and products derived therefrom. Many domesticated animals are known in the art. In other embodiments, the invention provides fungicidal compositions that are used, inter alia, for wound dressings. Many wound dressings are known in the art. The invention provides fabrics that resist pathogens or contaminants that respond to the enzyme systems disclosed herein. The fabrics comprise the fungicidal compositions described herein.

Some embodiments of the invention provides compositions and methods for reducing human infections. This is accomplished, for the first time, by a multicomponent composition comprising a hydrogen peroxide producing (HPP) enzyme and a free radical producing (FRP) enzyme in magnetic nanoparticles in one component and substrates for the enzymes in another component. The solid compositions are stable and inactive. Thus, they may be stored prior to or after incorporation into products. When the fungicidal activities are required, the multicomponent compositions are activated by hydration. The HPP enzyme acts on substrates to produce hydrogen peroxide and D-glucono-δ-lactone. The FRP enzyme acts on the hydrogen peroxide and one or more further substrates to produce free radicals. The hydrogen peroxide and free radicals have fungicidal properties.

In order that the invention described herein may be more fully understood, the following examples are set forth. It should be understood that these examples are for illustrative purposes only and are not to be construed as limiting this invention in any manner.

Example 1—Microbiocidal Optimization of Dry Enzyme and Substrate Disks

Materials and Methods

Five different lactoperoxidase (LP) to glucose oxidase (GOx) molar ratios were analyzed in dry enzyme disks to determine the optimal enzyme ratio for maximizing bactericidal activity. Two different concentrations of substrates in the dry substrate disks were also analyzed. These analyses were performed in-vitro on the bacterium *Xanthomonas campestris* pv. vitians isolate '09131A' which was originally collected in New York State and isolated and identified by Christine Smart, Professor of Plant Pathology at Cornell University. (http://blogs.cornell.edu/smartlab/.)

A second analysis was done to determine the optimal enzyme concentration to inhibit fungal growth. Four concentrations of enzymes were analyzed in dry enzyme disks to determine the optimal enzyme concentration to maximize fungicidal activity. All analyses were performed in-vitro on plant-pathogenic microorganism cultures obtained from collaborators in the Cornell University Section of Plant Pathology and Plant-Microbe Biology (Cornell University, Ithaca, N.Y.). The fungi *Rhizoctonia solani* (isolate 'AC1-A1') and *Fusarium graminearum* (isolate 'GZ014NY98') were collected in New York State isolated and identified by Professors Eric Nelson and Gary Bergstrom, respectively. The oomycete *Pythium ultimum* (isolate 'Geneva16') was collected in New York State and isolated and identified by Professor Eric Nelson. https://pppmb.cals.cornell.edu/people/eric-nelson.

A third analysis was done to determine the optimal enzyme concentration to inhibit oomycete growth. Three concentrations of enzymes were analyzed to determine optimal activity against oomycetes. The oomycete *Pythium ultimum* (isolate 'Geneva16') was collected in New York State and isolated and identified by Professor Eric Nelson (Cornell University, Ithaca, N.Y.).

For the optimization of enzyme ratios for bactericidal activity, lactoperoxidase (LP) and glucose oxidase (GOx) enzymes were immobilized in five different LP:GOx molar ratios (see Table 1). Dry enzyme disk compositions were the same as those listed in Example 2 (Table 2) with the exception of enzyme concentrations, which are listed in Table 1. Having a 1:1 LP:GOx enzyme disk was considered as a standard, therefore GOx concentrations were decreased proportionally to create 10:1 and 5:1 disks and LP concentrations were decreased proportionally to create the 1:5 and 1:10 disks. Magnetic nanoparticles (pH 3) were mixed with LP+GOx enzyme mixtures (pH 7.4) in a 1:1 volume ratio to immobilize enzymes. Nanoparticle concentrations were adjusted to maintain a 30% enzyme:nanoparticle mass ratio (Table 1). Two dry substrate disk formulations that were analyzed, called 1× and 10×, are listed in Table 2. Enzyme disk and substrate disk components were mixed with distilled deionized $H_2O$ to achieve desired concentrations, and dried under vacuum with a desiccant to remove $H_2O$. This process was repeated for the creation of all dry enzyme and substrate disks.

Magnetic nanoparticles were made and used for the molecular entrapment of peroxidase as described in US20150252352; PCT/US16/31419; and Corgié et al., *Adv. Functional Materials* 22:1940-51 (2012). The foregoing are incorporated by reference herein in their entirety.

Analysis to optimize bactericidal efficacy of dry enzyme and substrate disk formulations was performed twice. Each treatment was performed in duplicate. There were a total of ten treatments included in the LP:GOx ratio optimization. Each of the five LP:GOx ratios was analyzed with 1× and 10× substrate disks. Each analysis also included controls of 1× and 10× substrate disks only. The analyses were set up by creating bacterial lawns of Xcv on 85-mm petri dishes containing LB agar. 100 µl of $1 \times 10^7$ CFU/ml bacterial suspension was dispensed onto each dish ($1 \times 10^6$ CFU per plate), which contained three sterile glass beads. The beads were swirled to spread the inoculum evenly across the surface of the plate. Dry substrate disks were then placed in the center of each plate using sterile forceps. Dry enzyme disks were then placed on top of the dry substrate disks and each plate was wrapped with parafilm and incubated at 26.7° C. Zones of inhibition surrounding each treatment disk were measured after three days. Data were analyzed by analysis of variance in R Studio version 3.3.0 (R Studio, Boston, Mass.) using packages lme4 and lsmeans, and mean separations were done using Tukey's honest significant difference analysis. Means were considered significantly different at $P<0.05$.

TABLE 1

Optimization of lactoperoxidase and glucose oxidase in dry enzyme disks

| LP:GOx molar ratio | LP conc (µg/ml) | GOx conc. (µg/ml) | Nanoparticle conc. (mg/ml) | Enzyme conc. in dry disks (nM) |
|---|---|---|---|---|
| 10:1 | 125 | 25.8 | 0.503 | 94 |
| 5:1 | 125 | 51.6 | 0.589 | 110 |
| 1:1 | 125 | 258 | 1.277 | 238 |
| 1:5 | 25 | 258 | 0.943 | 176 |
| 1:10 | 12.5 | 258 | 0.902 | 168 |

TABLE 2

Dry substrate disk compositions

| Component | 1X concentration | 10X concentration |
|---|---|---|
| Potassium iodide | 0.3 mM | 3 mM |
| Ammonium thiocyanate | 0.5 mM | 5 mM |
| Carboxymethyl cellulose | 0.7% | 0.7% |
| Glucose | 50 mM | 500 mM |

To optimize enzyme concentrations for activity against fungi, four enzyme concentrations (1×, 2×, 5×, and 10×) were analyzed in a 1:1 molar ratio of LP:GOx. LP at 1250 µg/ml and GOx at 2580 µg/ml were mixed in a 1:1 ratio (pH 7.4) and the LP+GOx suspension was combined with nanoparticles at 12.77 mg/ml (pH 3) in a 1:1 enzyme:NP volume ratio. Proportional volumes of immobilized enzymes were then added to enzyme disk components listed in Example 2 (see Table 3) to achieve the following enzyme concentrations: 1×=238 nM; 2×=476 nM; 5×=1190 nM; and 10×=2380 nM. Disks were dried under vacuum prior to use.

The dry enzyme disks were analyzed for efficacy against *R. solani* and *F. graminearum*. 10× substrate disks (Table 2) were placed on the center of 85-mm plates containing potato dextrose agar. Dry enzyme disks were then placed on top of substrate disks, one per plate, followed by a 7 mm fungal culture plug placed directly on top of the enzyme disk mycelia side down. Fungal colony diameters were measured after five days (*R. solani*) and six days (*F. graminearum*).

To optimize activity against oomycetes, three enzyme concentrations (0.0017×, 0.34×, 1× in a 1:1 molar ratio of LP:GOx) were analyzed. Enzymes were immobilized as previously described and proportional volumes of immobilized enzymes were then added to enzyme disk components listed in Example 2 (Table 3) to achieve the following enzyme concentrations: 0.0034×=0.8 nM; 0.68×=161 nM; and 2×=476 nM. Disks were dried prior to use.

The dry enzyme disks were analyzed for efficacy against *P. ultimum*. 10× substrate disks (see Table 2) were placed on the center of 85-mm plates containing potato dextrose agar. Dry enzyme disks were then placed on top of substrate disks, one per plate, followed by a 7 mm fungal culture plug placed directly on top of the enzyme disk mycelia side down. Oomycete colony diameters were measured after five days.

Bactericidal Enzyme Ratio Optimization

Figure 1B:
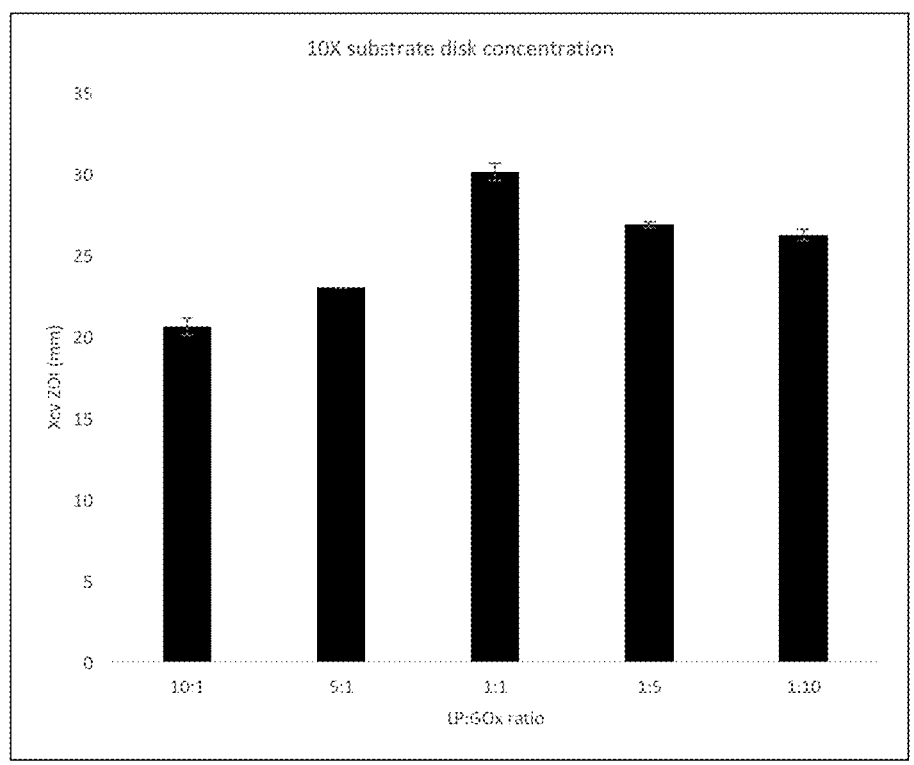
Figure 1C:
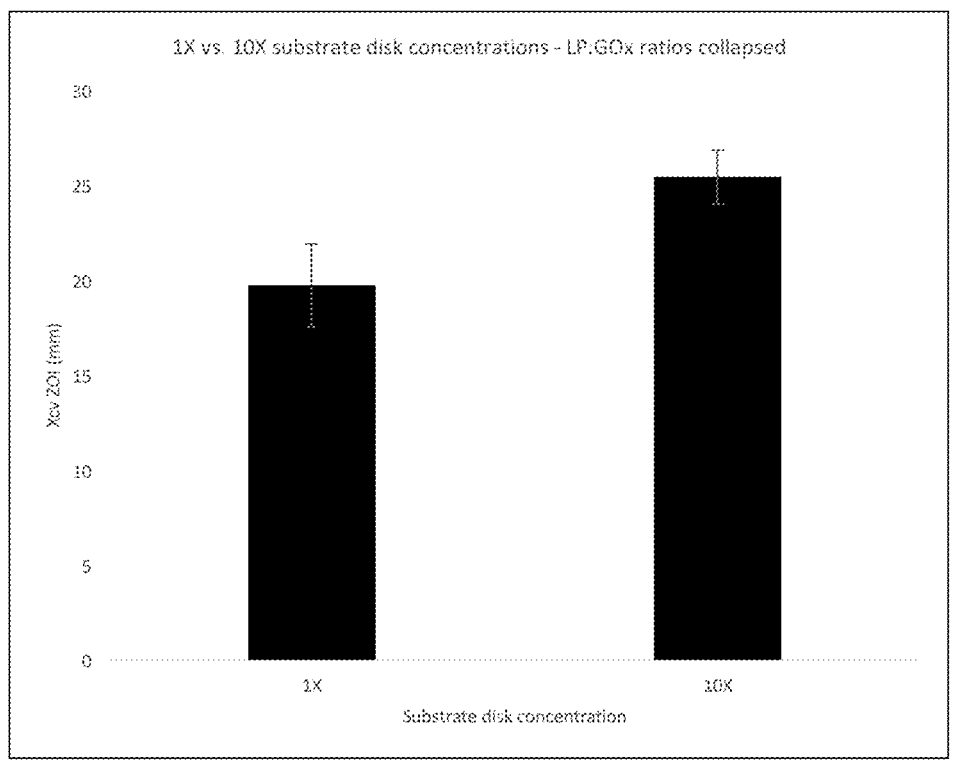

When LP:GOx ratios were analyzed using the 1× substrate concentration, the 1:1 ratio and ratios favoring higher GOx concentrations resulted in the largest zones of inhibition of Xcv (FIG. 1A). This result was not statistically significant based on analysis of variance and Tukey's honestly significant difference (Tukey's HSD, P<0.05) in a first analysis, but was significant in a second analysis with the exception of the 1:10 ratio. A similar pattern was observed when LP:GOx ratios were analyzed using the 10× substrate concentration (see FIG. 1B). In analysis 2, the 1:1 ratio resulted in significantly larger zones of inhibition compared to all other treatments. Ratios of 1:5 and 1:10 also had significantly more efficacy than the 10:1 and 5:1 ratios. The 10× substrate concentration resulted in significantly larger zones of inhibition than the 1× substrate concentration in both analysis (see FIG. 1C). Optimal dry enzyme and substrate disk formulae for maximizing bactericidal efficacy was determined to be a 1:1 LP:GOx molar ratio and 10× substrate concentration.

Fungicidal Enzyme Concentration Optimization

Figure 2:
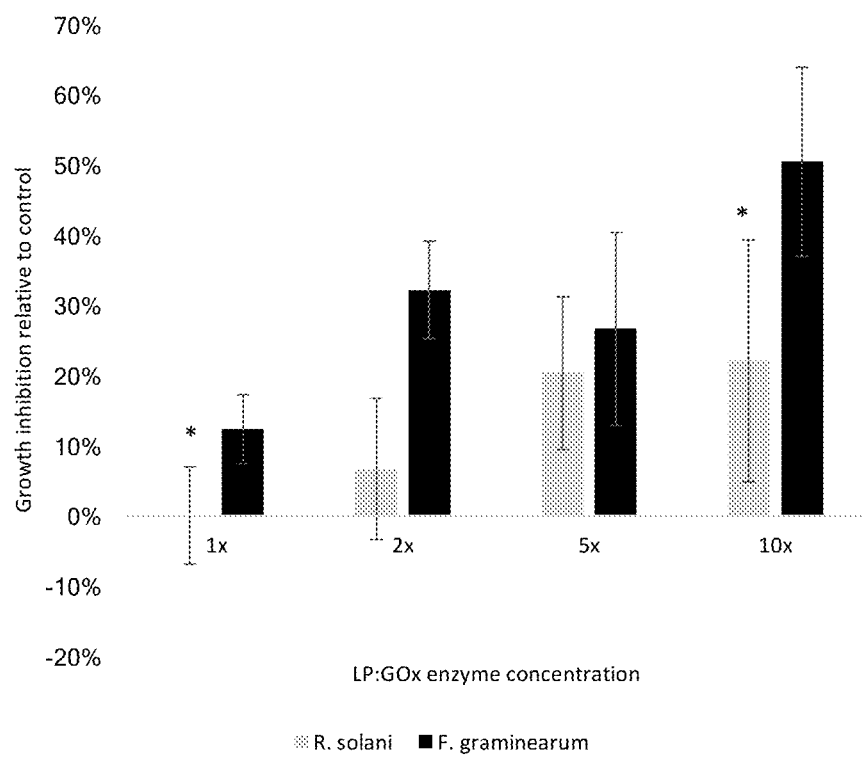
FIG. 2. Effect of LP:GOx enzyme concentration on dry enzyme disk efficacy against fungal growth (*Rhizoctonia solani* and *Fusarium graminearum*). Each bar represents the mean of two replicates. Columns with an asterisk above them are significantly different (Tukey's HSD, P<0.05).

*Fusarium graminearum* was more sensitive to the dry enzyme disks than *Rhizoctonia solani* (see FIG. 2). There was a pattern of increasing growth suppression with increasing enzyme concentration observed for both *F. graminearum* and *R. solani*. Due to high variance among replicates, few of the observed differences were statistically significant (Tukey's HSD, P<0.05). *Rhizoctonia solani* growth was inhibited significantly more at the 10× concentration than the 1× concentration (see FIG. 2). Overall, there was a dose effect of LP:GOx enzyme concentration on fungal growth, and the 10× enzyme concentration resulted in the greatest inhibitory effect by reducing growth of *R. solani* and *F. graminearum* by 22% and 50%, respectively.

Optimization of Activity Against Oomycetes

Figure 3:
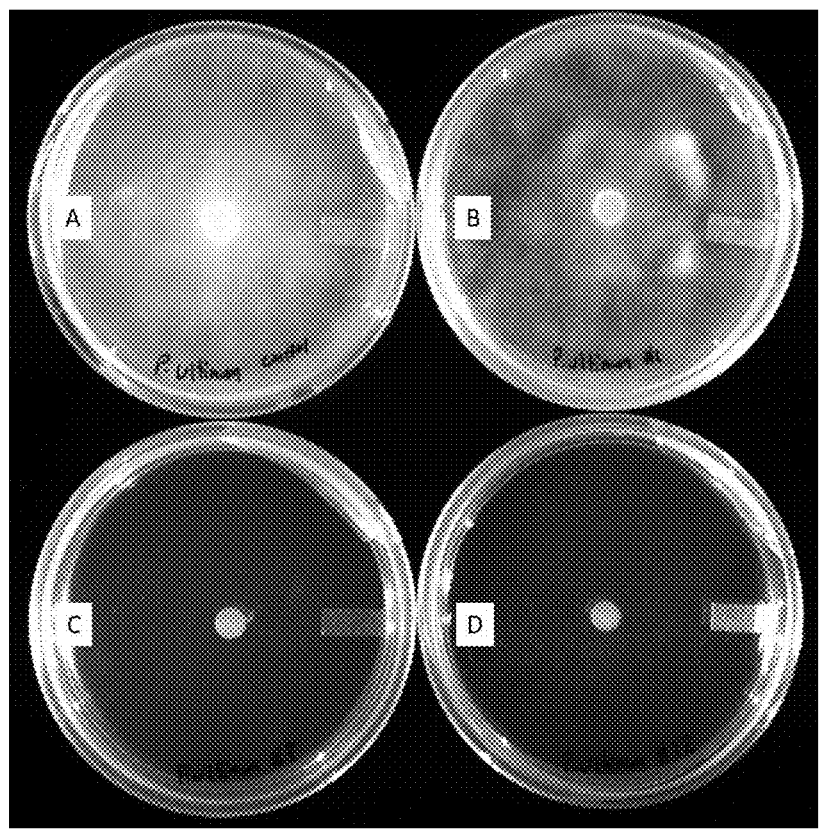
FIG. 3. Effect of three LP:GOx enzyme concentrations on growth of *Pythium ultimum*. Plate A is a control with dry substrate disk only. Plate B shows that the lowest enzyme concentration (0.0034× or 0.8 nM enzyme) did not inhibit growth of *P. ultimum* relative to the control. Plate C shows a medium enzyme concentration (0.68× or 161 nM enzyme) completely inhibited *P. ultimum* growth. Plate D shows a high enzyme concentration (2× or 476 nM enzyme) also completely inhibited *P. ultimum* growth.

Three LP:GOx concentrations were analyzed in dry enzyme disks for their efficacy against *P. ultimum*. The lowest concentration (0.0034×) did not inhibit *P. ultimum* growth relative to the control; however, the 0.68× and 2× concentrations both killed the culture plugs, effectively reducing growth by 100% (see FIG. 3).

Example 2—Synergy Between Chemical Fungicides and Immobilized LP:GOx

Materials and Methods

The effect of combining commercial chemical fungicide with immobilized enzymes on microbial growth was analyzed in-vitro on two species of oomycete plant pathogens belonging to the genus *Pythium*. One isolate each of *Pythium ultimum* (isolate 'Geneva 16') and *Pythium aphanidermatum* (isolate 'Pa58') were both collected in New York State and isolated and identified by Professor Eric Nelson (Cornell University Section of Plant Pathology and Plant-Microbe Biology, Cornell University, Ithaca, N.Y.). https://pppmb.cals.cornell.edu/people/eric-nelson. Isolates were stored on corn meal agar (CMA).

A suspension of lactoperoxidase (LP) and glucose oxidase (GOx) was prepared in a 1:1 M ratio at a concentration of 1.613 μM and pH 7.4. Enzymes were immobilized by combining the 1.613 μM enzyme suspension with a 1.277 mg/ml nanoparticle (NP) suspension (pH 3) in a 1:1 volume ratio. Immobilized enzymes were then combined with solid substrate components as described in Table 3. Separate dry substrate disks were made according to the substrate disk compositions listed in Table 3. Liquid enzyme and substrate disk suspensions were dispensed onto parafilm in 50 μl aliquots and dried under vacuum for approximately 1 hour. Dry enzyme and substrate disks were stored at ambient temperature (approximately 22° C.).

Daconil® fungicide (chlorothalonil 26.6%, manufactured by GardenTech, Palatine, Ill., purchased from Amazon, Seattle, Wash. cat. no. B000RUGIY0).) Daconil® was mixed with sterile DDI $H_2O$ to create a series of 4 dilutions (0.78% Daconil®, 0.078% Daconil®, 0.039% Daconil®, 0.0078% Daconil®). The highest concentration analyzed (0.78% Daconil®) is twice the highest label rate for vegetables, and was just below the half maximal effective concentration ($EC_{50}$) value for Daconil® on *Pythium ultimum*. The $EC_{50}$ is defined as the concentration of fungicide that induces a response halfway between the baseline and maximum response. The $EC_{50}$ value for Daconil® on *Pythium ultimum* was 0.2% based on regression analysis of the data shown in FIG. 5. Based on the regression it was estimated that the full fungicidal concentration is approximately 5% Daconil®.

Fungicides were applied to the center of an 85 mm petri dish containing CMA by stacking two sterile 7 mm filter paper discs on the center of each plate and applying 50 μl of fungicide solution or sterile DDI $H_2O$ (control) to the stacked discs. Treatments that included Daconil®+immobilized enzyme disks were prepared by placing, in a stack on the center of each CMA plate, one substrate disk, one enzyme disk, and 2 filter paper discs with 50 μl fungicide applied as the last step. A 7 mm plug of actively growing *Pythium* mycelia was placed, mycelia side down, directly on top of the treatment at the center of each plate. The entire analysis was done once for *Pythium ultimum* and *Pythium aphanidermatum*.

Treatments were as follows:
Daconil® (0.78%) only
Daconil® (0.078%) only
Daconil® (0.039%) only
Daconil® (0.0078%) only
Control—$H_2O$ on filter paper
Control—1 dry enzyme disk and 1 dry substrate disk+$H_2O$ on filter paper
Daconil® (0.78%)+1 dry enzyme disk and 1 dry substrate disk
Daconil® (0.078%)+1 dry enzyme disk and 1 dry substrate disk
Daconil® (0.039%)+1 dry enzyme disk and 1 dry substrate disk
Daconil® (0.0078%)+1 dry enzyme disk and 1 dry substrate disk Plates were stored on the bench and colonies allowed to grow for 2 days before two perpendicular colony diameter measurements per plate were recorded. The two perpendicular measurements were averaged for each plate.

TABLE 3

Solid immobilized enzyme and substrate disk compositions

| Enzyme disk composition | | Substrate disk composition | |
| --- | --- | --- | --- |
| Component | Concentration | Component | Concentration |
| Potassium iodide | 0.3 mM | Potassium iodide | 0.3 mM |
| Ammonium thiocyanate | 0.5 mM | Ammonium thiocyanate | 0.4 mM |
| Carboxymethyl cellulose | 0.7% | Carboxymethyl cellulose | 0.7% |
| LP + GOx (1:1 ratio) | 81 nM | Avicel | 2.0% |
| | | Glucose | 50M |

Figure 4:
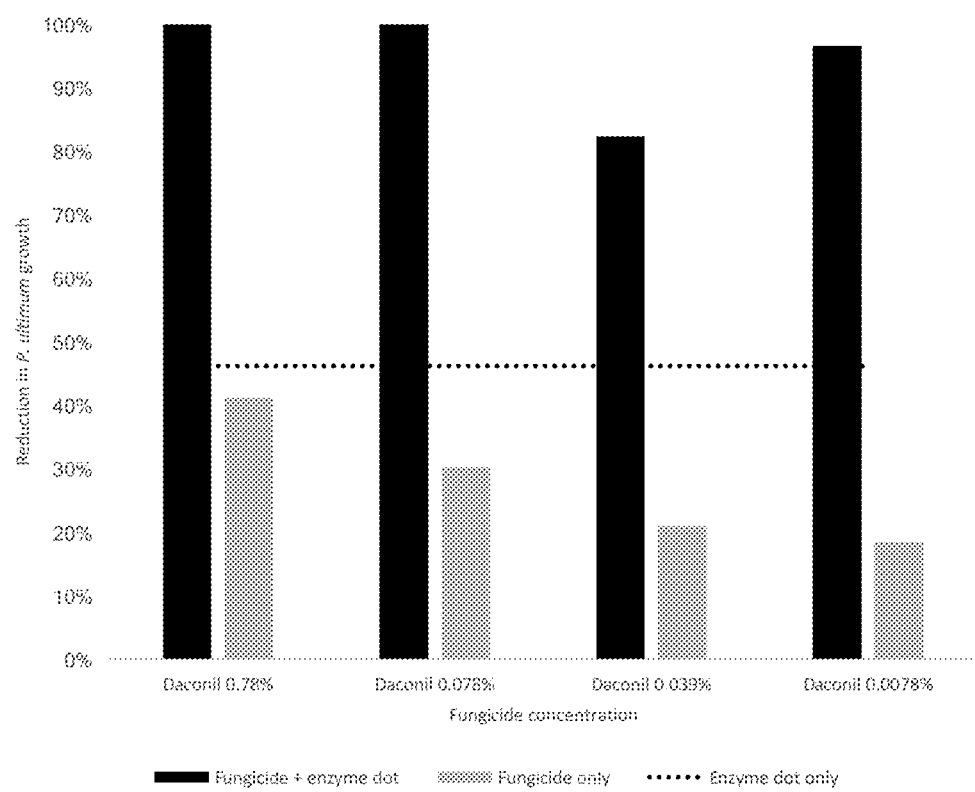
FIG. 4. Reduction in *P. ultimum* growth relative to the untreated control following treatment by Daconil®+enzyme disk (black bars), Daconil® only (gray bars), and enzyme disk only (dotted line). Enzymes concentrations in enzyme disks were 81 nM.
Figure 5:
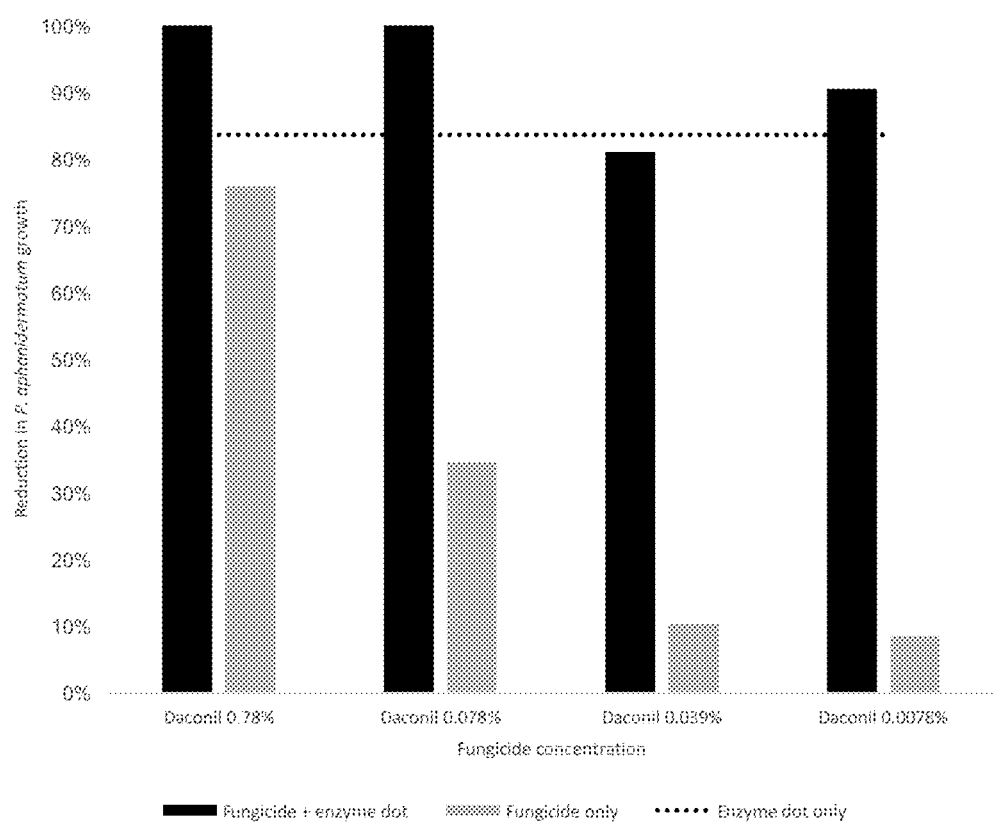
FIG. 5. Reduction in *P. aphanidermatum* growth relative to the untreated control following treatment by Daconil®+enzyme disk (black bars), Daconil® only (gray bars), and enzyme disk only (dotted line). Enzymes concentrations in enzyme disks were 81 nM.
Figure 6:
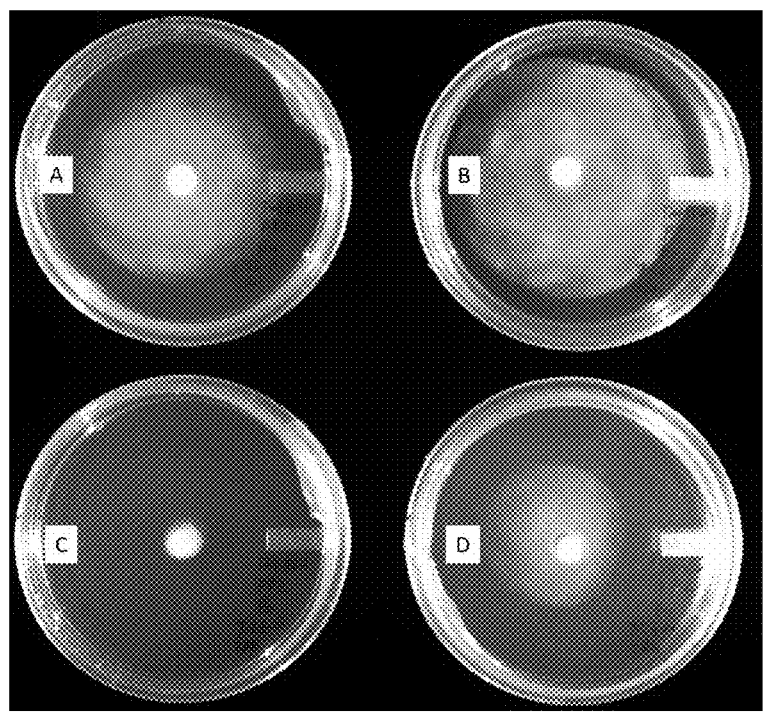
FIG. 6. Reduction in *P. ultimum* growth following treatment by Daconil®, enzyme disk, and Daconil®+enzyme disk. Enzyme concentrations in enzyme disks were 81 nM. Smaller colony diameters indicate greater oomycete growth inhibition. Plate A shows that a Daconil®-only treatment (0.0078% Daconil®) resulted in an 18% reduction in growth relative to the non-treated control. Plate B shows a non-treated control. Plate C shows that a 0.0078% Daconil®+ enzyme disk treatment resulted in a 97% reduction in growth relative to the non-treated control, and a 32% synergistic effect compared to the additive effects of fungicide-only and enzyme disk-only treatments. Plate D shows that an enzyme disk-only treatment resulted in a 46% reduction in growth relative to the non-treated control.
Figure 7:
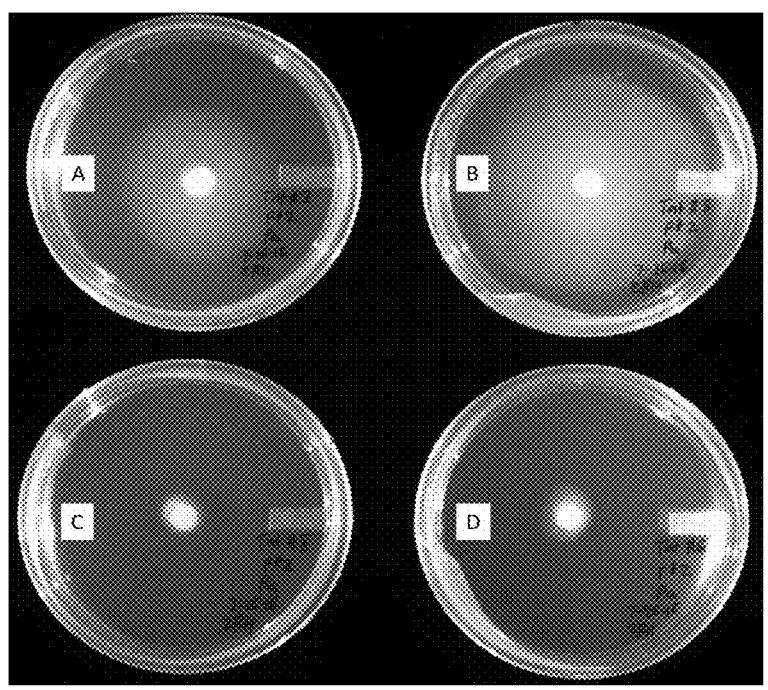
FIG. 7. Reduction in *P. aphanidermatum* growth following treatment by Daconil®, enzyme disk, and Daconil®+enzyme disk. Enzymes concentrations in enzyme disks were 81 nM. Plate A shows that a Daconil®-only treatment (0.078% Daconil®) resulted in a 34% reduction in growth relative to the non-treated control. Plate B shows a non-treated control. Plate C shows that a 0.078% Daconil®+ enzyme disk treatment resulted in a 100% reduction in growth relative to the non-treated control. The small white halo surrounding the culture plug is due to the application of Daconil® and is not mycelial growth. Plate D shows that an Enzyme disk-only treatment resulted in an 84% reduction in growth relative to the non-treated control.
Figure 8:
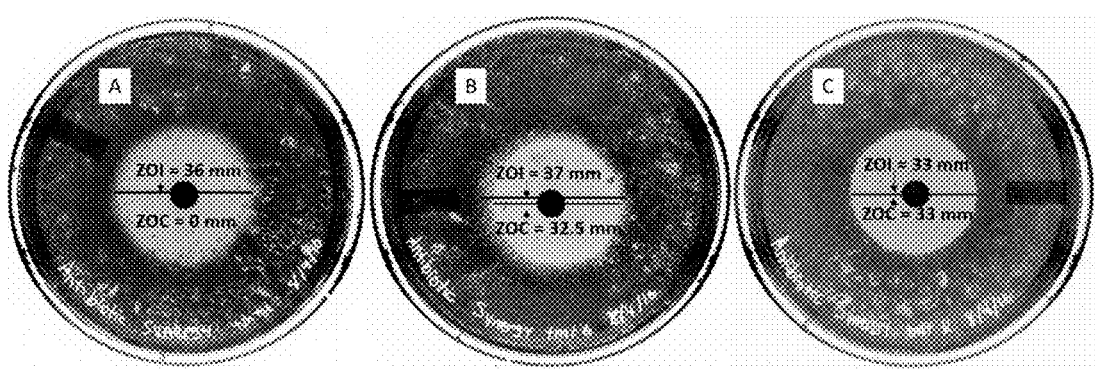
FIG. 8. Enhanced activity of ampicillin with dry enzyme disk against Xcv. Enzymes concentrations in enzyme disks were 238 nM. Plate A shows that 100 μg ampicillin alone resulted in a zone of interference (ZOI) of 36 mm and no zone of clearance (ZOC). Sparse ampicillin-resistant colonies can be seen throughout the ZOI. Plate B shows that a 100 μg ampicillin plus dry enzyme disk resulted in a ZOC of 32.5 mm and an additional ZOI that extended 4.5 mm beyond the edge of the ZOC. Plate C shows that a dry enzyme disk alone resulted in a ZOC of 33 mm with no ZOI beyond the ZOC boundary. Plates A-C are visualized using reverse black and white imaging to enhance growth visualization.
Figure 9:
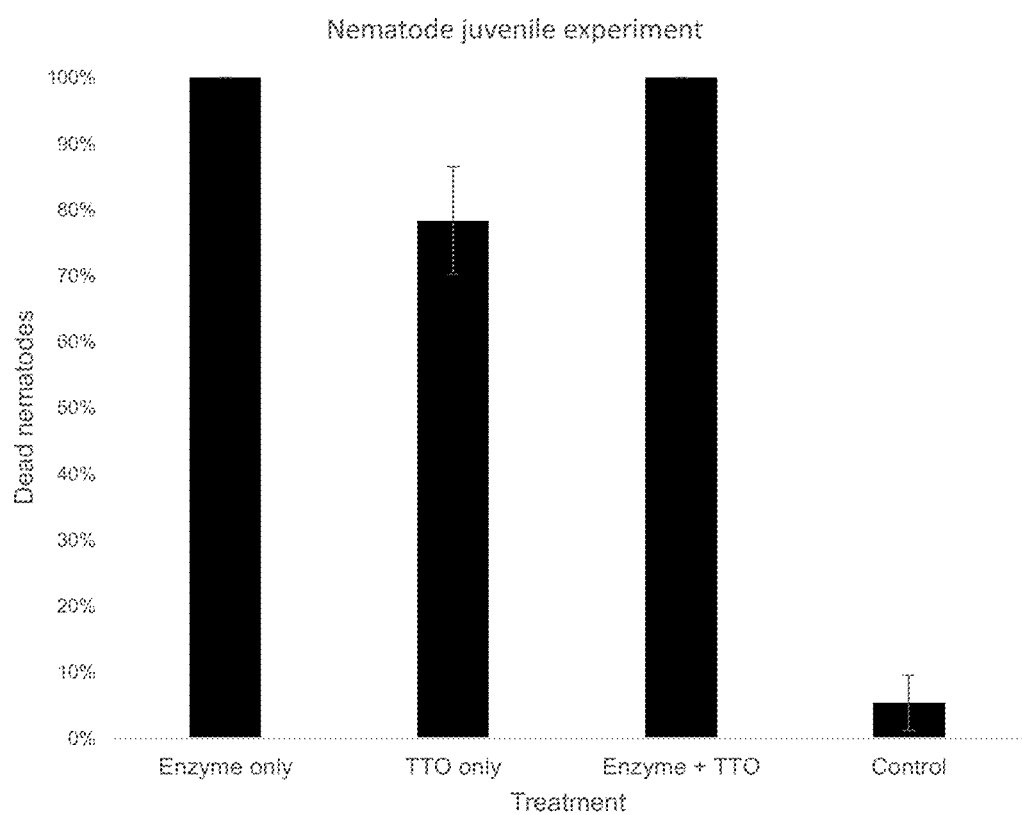
FIG. 9: Percent of nematodes killed after three-day treatment incubation. Each bar represents the mean of three replicates.
Figure 10A:
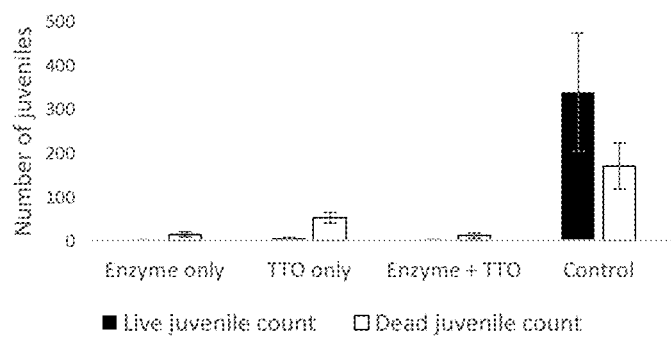
FIGS. 10A and 10B: Effect of treatments on nematodes hatching from cysts (FIG. 10A) and eggs (FIG. 10B). Black bars show live nematode juveniles counted and white bars show dead nematode juveniles counted. Each bar represents the mean of three replicates.
Figure 10B:
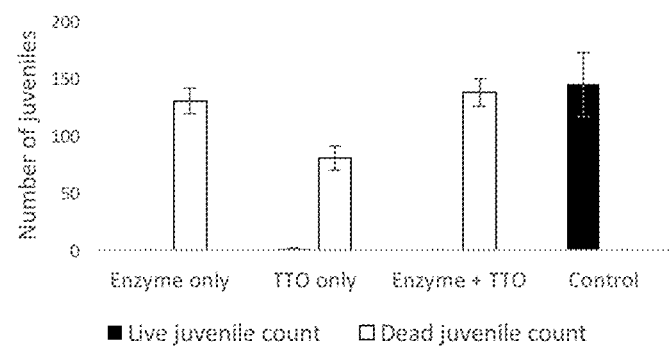

Daconil®+enzyme disk treatments resulted in increased suppression of *P. ultimum* and *P. aphanidermatum* compared to Daconil®-only and enzyme disk-only treatments (see FIGS. 4, 5, 6, and 7). The additive effect of Daconil®+enzyme disk was calculated by adding together the reduction in growth due to Daconil® only and the reduction in growth due to enzyme disk only. The enzyme disk-only treatment resulted in a 46% and 84% reduction in *P. ultimum* and *P. aphanidermatum* growth, respectively. The additive effect of Daconil®+enzyme disk exceeded 100% for *P. aphanidermatum* due to its high sensitivity to the enzyme disk. Therefore, the additive and synergistic effects are only reported for *P. ultimum* (see FIG. 4). Synergistic activity of Daconil®+enzyme disk on *P. ultimum* ranged from a 13% increase in growth suppression at the highest Daconil® concentration to 32% growth suppression at the lowest Daconil® concentration. Synergism between Daconil® and enzyme disk was observed in each of the four Daconil® concentrations analyzed on *P. ultimum* (see FIG. 4). Values reported in FIGS. 4 and 5 are the percent reduction in *Pythium* growth relative to the untreated control.

In-vitro exposure of *P. ultimum* and *P. aphanidermatum* to the commercial chemical fungicide Daconil® at four concentrations, enzyme disk only, and Daconil®+enzyme disk resulted in reduced mycelial growth in every treatment relative to the untreated control. The effect of the solid substrate disk only and sterile filter paper+H$_2$O were analyzed as controls and neither were found to inhibit mycelial growth. The synergistic effect of the combination of Daconil®® and enzyme disk on inhibition of *P. ultimum* was observed at all four Daconil®® concentrations used (see FIG. 4). This showed that Daconil®, or chlorothalonil-containing products, had enhanced efficacy through the inclusion of immobilized enzyme disk. Additionally, less chemical fungicide may be used in the presence of enzyme disks to achieve the same level of fungal suppression or disease control as higher fungicide application rates in the absence of enzyme disks.

Synergism between Daconil® and enzyme disks could not be calculated for *P. aphanidermatum* due to the high sensitivity of this species to the enzyme disk used in this analysis. However, treatments of Daconil®+enzyme disk consistently resulted in greater suppression of *P. aphanidermatum* growth compared to treatments of Daconil® only and enzyme disk only (see FIG. 5). The effect of lower enzyme concentrations of LP:GOx in immobilized enzyme disks with and without Daconil® on *P. aphanidermatum* may also be analyzed.

Example 3—Synergy Between Antibiotics and Immobilized LP:GOx

Materials and Methods

Antibiotic suspensions (ampicillin) were diluted to four concentrations so that the final amounts applied to sterile filter paper disks were 0.1 μg, 1 μg, 10 μg and 100 μg. The minimum inhibitory concentration (MIC) of ampicillin for *Xanthomonas campestris* was estimated to be between 10 μg and 50 μg. The MIC is defined as the lowest concentration of antibiotic that completely inhibits growth of the bacteria being evaluated and the minimum bactericidal concentration (MBC) is defined as the lowest concentration of antibiotic at which bacteria are killed. This was not determined for *Xanthomonas campestris* because resistant colonies persisted at the highest antibiotic concentration. Dry enzyme disks were made according to the formula in Table 3 with the exception of the enzyme concentration which is 238 nM. 10× dry substrate disks were made according to the formula in Table 2. The following treatments were analyzed:

0.1 μg antibiotic only
1 μg antibiotic only
10 μg antibiotic only
100 μg antibiotic only
Control—sterile DDI $H_2O$ on filter paper
Control—1 dry enzyme disk and 1 dry substrate disk+sterile DDI $H_2O$ on filter paper
Control—1 dry substrate disk+sterile DDI $H_2O$ on filter paper
0.1 μg antibiotic+1 dry enzyme disk and 1 dry substrate disk
1 μg antibiotic only+1 dry enzyme disk and 1 dry substrate disk
10 μg antibiotic only+1 dry enzyme disk and 1 dry substrate disk
100 μg antibiotic only+1 dry enzyme disk and 1 dry substrate disk The analysis was performed by creating bacterial lawns of Xcv on 85-mm perti dishes as described in Example 1. It followed the methods described in Example 2 with the exception of using antibiotic suspensions at four concentrations instead of fungicides. It also measured zones of inhibition of bacterial growth after two days rather than placing 7-mm fungal plugs on top of the treatments and measuring colony diameters.

Results:

Of the four ampicillin-alone treatments, only the 100 μg ampicillin-alone treatment inhibited the growth of Xcv. This treatment resulted in a ZOI of 36 mm (FIG. 8). 100 μg ampicillin-alone did not result in a ZOC and ampicillin-resistant bacterial colonies could be seen throughout the 36 mm ZOI (FIG. 8). All four of the ampicillin+dry enzyme disk treatments resulted in ZOC ranging from 31 mm to 33.5 mm (Table 4). The 100 μg ampicillin+dry enzyme disk treatment resulted in a ZOC of 32.5 mm with an additional ZOI extending beyond the boundary of the ZOC by an additional 4.5 mm. The 100 μg ampicillin+dry enzyme disk treatment resulted in a greater inhibitory effect against Xcv than either ampicillin alone or enzyme disk alone by clearing all viable bacteria in the ZOC surrounding the treatment and by inhibiting bacterial growth beyond the ZOC. The controls without enzyme did not inhibit growth of Xcv.

TABLE 4

Zones of clearance (ZOC) and zones of inhibition (ZOI) of Xcv surrounding ampicillin-alone and ampicillin + dry enzyme disk treatments.

| Treatment | ZOC (mm) | ZOI (mm) |
|---|---|---|
| 100 ug ampicillin | 0 | 36 |
| 10 ug ampicillin | 0 | 0 |
| 1 ug ampicillin | 0 | 0 |
| 0.1 ug ampicillin | 0 | 0 |
| Control - fp + H2O | 0 | 0 |
| 100 ug ampicillin + enzyme disk | 32.5 | 37 |
| 10 ug ampicillin + enzyme disk | 33.5 | 0 |
| 1 ug ampicillin + enzyme disk | 31 | 0 |
| 0.1 ug ampicillin + enzyme disk | 32.5 | 0 |
| Control - substrate disk + fp + H2O | 0 | 0 |
| Control - enzyme disk | 33 | 0 |

Example 4—Plant Pathogen Control Using Stabilized Biocidal Enzymes and Biocidal Vegetable Extracts Essential oils, such as tea tree oil, have antimicrobial properties. Tea tree oil (TTO) in combination with stabilized biocidal enzymes, controlled plant pathogens as shown using the plant pathogenic oomycete *Pythium ultimum*. Dilutions of TTO were impregnated into filter paper (FP) disks, combined with stabilized biocidal enzyme disks, and placed onto cornmeal agar plates with a plug of *P. ultimum* culture. The reduction in colony growth was measured and compared to colony growth in the absence of biocidal enzymes and TTO.

Materials and Methods

Stabilized biocidal enzyme disk preparation. Dry enzyme disks were made by combining 3 μl KI (1M), 5 μl $NH_4SCN$ (1M), 175 μl 4% carboxymethyl cellulose (CMC), 295 μl stabilized lactoperoxidase+glucose oxidase (LPO+GOx) (119 nM+152.2 nM), and 3 μl blue food dye brought up to a final volume of 1 ml with DDI $H_2O$. Enzyme stabilization was performed as follows: lactoperoxidase (LPO) (125

µg/ml, pH 7.4) and glucose oxidase (GOx) (330 µg/ml, pH 7.4) were mixed to achieve a 1:1.3 M LPO:GOx ratio and stored on ice. Magnetite nanoparticles (NP) (1.277 mg/ml, pH 3, approximately 5 ml stock) were ultrasonicated at 40% amplitude for 1 min, cooled to ambient temperature (approximately 21° C.) in a water bath, and pipette mixed with the LPO:GOx enzyme suspension in a 1:1 enzyme:NP ratio. Dry substrate disks were made my combining 30 µl KI (1M), 50 µl NH$_4$SCN (1M), 350 µl 4% CMC, 500 µl glucose (1M), and 3 µl red food dye brought up to a final volume of 1 ml with DDI H2O. Dyes were included to differentiate enzyme disks from the substrate disks and were not biologically active or structural components of the disks. Each solution was pipette mixed several times and vortexed briefly. Solutions were dispensed in 50 µl aliquots onto parafilm and dried at ambient temperature in a vacuum oven containing desiccant at −50 kPa. After approximately 2 hours, dry enzyme and substrate disks were stored in the dark at 4° C. until use.

Tea tree oil disk preparation and culture growth assay. Tea tree oil (Active Ingredient (AI): tea tree oil 100%, Mason Natural, Miami Lakes, Fla.) (TTO) was diluted in sterile DDI H$_2$O. Whatman® qualitative grade 1 filter paper (Sigma-Aldrich) was cut into 7 mm disks using a 3-hole punch, and disks were autoclaved prior to use. FP disks were impregnated with 5 µl of each of four TTO dilutions. Control FP disks were impregnated with 5 µl sterile DDI H$_2$O. TTO and enzyme disk interactions were tested by placing one substrate disk on the center of a petri dish containing corn meal agar, followed by one enzyme disk, one TTO-impregnated FP disk, and one culture plug mycelia-side down. Final enzyme concentrations in enzyme disks were 4 nM for *P. ultimum*. Culture plugs of *P. ultimum* measured 7 mm in diameter. Each experiment included the same TTO dilution series plated without substrate and enzyme disks, as well as a substrate+enzyme disk-only treatment and a non-treated control. All plates, including controls, contained a FP disk, and each treatment was replicated once. Plates were left on the bench at ambient temperature for 2 days. At that time, control colonies had nearly grown to the plate edge. Two perpendicular colony diameter measurements were recorded for *P. ultimum*.

Results

Tea tree oil combined with the stabilized enzyme formulation resulted in a statistically synergistic effect at the two lowest TTO concentrations and was additive at the two highest concentrations (Table 5). The combined effects were significantly greater than the effects of the enzyme formulation alone and three of the four TTO concentrations alone. The highest TTO concentration alone produced a significantly greater effect than enzyme formulation alone, and was not significantly different from any of the four combined effects (Table 5).

TABLE 5

Inhibition of *Pythium ultimum* by the stabilized LPO formulation alone and in combination with tea tree oil using TTO-impregnated filter paper disks.

| Tea tree oil dose | Reduction in growth[a] | | | | Tukey's HSD | Combined effect | |
|---|---|---|---|---|---|---|---|
| | (+) enzyme | SD | (−) enzyme | SD | | (observed − expected)[b] | Combination result |
| 30% | 100% a[c] | 0.0% | 91% a | 12.1% | 23.4% | 0% | additive |
| 20% | 100% a | 0.0% | 66% b | 9.4% | | +7% | additive |
| 15% | 100% a | 0.0% | 45% bc | 2.1% | | +28% | synergistic |
| 10% | 94% a | 6.6% | 31% c | 1.6% | | +36% | synergistic |
| 0% | 27% c | 4.7% | NA | NA | | | |

[a]Reduction in growth relative to non-treated controls. Each value is the mean of two replicates.
[b]Difference between observed effect of fungicide (+) enzyme formulation and expected additive effect. Expected value calculated by adding the effect of fungicide alone and the effect of the enzyme formulation alone for each fungicide concentration.
[c]Means followed by the same letter are not significantly different, Tukey's HSD (P < 0.0

Example 5—Pathogenic Nematode Control Using Biocidal Stabilized Enzymes and Stabilized Emulsified Tea Tree Oil Root-knot nematodes from the genus *Meloidogyne* infect a wide array of plants, including woody crops and vegetables, causing yield loss. The cyst nematode *Heterodera schachtii* causes growth retardation in infected plants and can cause massive yield loss at high population densities. Control of nematode populations is vital to reducing losses associated with reduced crop yields. Stabilized biocidal enzymes combined with TTO control plant pathogens but TTO is not miscible in water and difficult to combine with biocidal enzymes. In this example, microencapsulated TTO was combined with stabilized biocidal enzymes for the control of plant pathogens. Nematode juveniles, eggs, and cysts were incubated with treatments containing biocidal stabilized enzymes, TTO, or both, to measure plant pathogenic nematodes killing or control.

Materials and Methods

Preparation of microencapsulated TTO and stabilized biocidal enzymes. Stabilized microencapsulated TTO (40%, 40× strength) was prepared by combining 2 ml of a 2% (w/w) solution of EHM (Ethyl hydroxyethyl cellulose EHM300, Akzonobel), 4 ml TTO (pure), and 4 ml DDI H$_2$O. This solution was sonicated two times for 1 minute each at 40% amplitude. ¼th inch horn. The 20×TTO substrate solution was made by combining 100 µl stabilized EHM TTO mix (40% TTO), 500 µl glucose (1M), 3 µl red food dye, and brought up to a final volume of 1 ml with DDI H$_2$O. The standard substrate solution was made by combining 500 µl glucose (1M), 3 µl red food coloring dye, and brought up to a final volume of 1 ml with DDI H$_2$O. The enzyme solution was made by combining 3 µl KI (1M), 5 µl NH$_4$SCN (1M), 70 µl 4% carboxymethyl cellulose (CMC), 295 µl stabilized lactoperoxidase+glucose oxidase (LPO+GOx) (119 nM+152.2 nM), and 3 µl blue food dye brought up to a final volume of 1 ml with DDI H$_2$O. Enzyme stabilization was performed as follows: LPO (125 µg/ml, pH 7.4) and GOx (330 µg/ml, pH 7.4) were mixed to achieve a 1:1.3 M LPO:GOx ratio and stored on ice. Magnetite nanoparticles (NP) (1.277 mg/ml, pH 3, approximately 5 ml stock) were ultrasonicated at 40% amplitude for 1 min, cooled to ambient temperature (approximately 21° C.) in a water bath, and pipette mixed with the LPO:GOx enzyme suspension in a 1:1 enzyme:NP ratio. Each solution was pipette mixed several times and vortexed briefly. Solutions were stored in the dark at 4° C. until use.

Control of plant pathogenic nematodes using microencapsulated TTO and stabilized biocidal enzymes. For the nematode juvenile analyses, a stock suspension of *Meloidogyne incognita* juveniles was prepared at a concentration of 300 juveniles/ml. Four treatment solutions were prepared as follows (1 ml total volume): Treatment solution (Tmt) 1=33 µl enzyme solution (1.96 nM lactoperoxidase+2.51 nM glucose oxidase)+33 µl standard substrate solution (500 mM glucose)+934 µl water, Tmt 2=33 μl 0.066% tea tree oil (TTO) solution+967 μl water, Tmt 3=33 μl enzyme solution (1.96 nM lactoperoxidase+2.51 nM glucose oxidase)+33 μl 0.066% TTO solution+934 μl water, and Tmt 4 (control)=1000 μl water. Each treatment solution was combined with 1 ml of the *M. incognita* stock suspension in a 10 ml beaker for 300 juveniles per experiment. Analyses were triplicated for each treatment resulting in 12 samples in total. They were stored individually in tightly sealed boxes to reduce volume loss due to evaporation at room temperature for three days. After three days, 100 juveniles were removed from each sample and counted as live or dead. If movement was observed during the count, the juvenile was counted as alive. If no movement was observed, the juvenile was counted as dead.

In the nematode cyst analyses, each sample (10 ml beaker) received approximately 50 *Heterodera schachtii* cysts. Cysts were hand-picked under a dissecting microscope and added to each beaker. Four treatment solutions were prepared as follows (2 ml total volume): Tmt 1=33 μl enzyme solution (1.96 nM lactoperoxidase+2.51 nM glucose oxidase)+33 μl standard substrate solution (500 mM glucose)+1934 μl water, Tmt2=33 μl 0.066% tea tree oil (TTO) solution+1967 μl water, Tmt3=33 μl enzyme solution (1.96 nM lactoperoxidase+2.51 nM glucose oxidase)+33 μl 0.066% TTO solution+1934 μl water, and Tmt4 (control)=2000 μl water. Each sample with 50 cysts received 2 ml of treatment solution (2 ml total experimental volume). Analyses were triplicated for each treatment resulting in 12 samples in total. Samples were stored individually in boxes at room temperature for 1 week. After 1 week, 300 μl of the sample volume was removed and the number of live or dead juveniles was counted as previously described.

In the nematode egg analyses, a stock suspension of *H. schachtii* eggs was prepared at a concentration of 1200 eggs/ml. Each sample (10 ml beaker) received 800 μl of the egg suspension for 960 eggs per experimental unit. Four treatment solutions were prepared as follows (1.2 ml total volume): Tmt1=33 μl enzyme solution (1.96 nM lactoperoxidase+2.51 nM glucose oxidase)+33 μl standard substrate solution (500 mM glucose)+1134 μl water, Tmt2=33 μl 0.066% tea tree oil (TTO) solution+1167 μl water, Tmt3=33 μl enzyme solution (1.96 nM lactoperoxidase+2.51 nM glucose oxidase)+33 μl 0.066% TTO solution+1134 μl water, and Tmt4 (control)=1200 μl water. Each sample with 800 μl *H. schachii* egg suspension received 1.2 ml of treatment solution (2 ml total experimental volume). Analyses were triplicated for each treatment resulting in 12 samples in total. Samples were stored individually in boxes at room temperature for 1 week. After 1 week, 300 μl of the sample volume was removed and the number of live or dead juveniles was counted as previously described.

Results

Results from each of the analyses showed effective control of nematodes by stabilized enzymes. FIG. 9 shows the result of the nematode juvenile experiment for which the treatments with stabilized enzymes alone and stabilized enzymes with tea tree oil showed 100% effectiveness at killing M. incognita juveniles. 78% of the nematode juveniles were killed in a solution of tea tree oil alone. Only 5% of nematode juveniles were killed in the control sample.

FIGS. 10A and 10B show the results of the nematode egg and cyst analyses. In FIG. 10A, the total number of nematode juveniles hatched from *H. schachtii* cysts, both live and dead, observed in the treatments with stabilized enzymes, TTO, or both is greatly reduced from the total number of nematodes observed in the control solution. The treatments inhibit hatching from the cysts. The enzyme treatment is more inhibitory to hatching than TTO alone. Juveniles that do hatch from cysts following treatment are nearly all dead by the end of the incubation period. FIG. 10B shows the number of nematode juveniles hatched from eggs, both live and dead, observed in the treatments with stabilized enzymes, TTO, or both. In this case, the treatments do not inhibit hatching, though the juveniles that do hatch are subsequently killed by the treatments during the incubation period.

Example 6—Plant Pathogen Control Using Stabilized Biocidal Enzymes and Mancozeb Mancozeb is a non-systemic fungicide used for agriculture to control fungal diseases in a wide array of field crops. An enhanced fungicidal effect from the combination of mancozeb and stabilized biocidal enzymes was shown. Solid culture growth media was amended with mancozeb at four concentrations. Stabilized biocidal enzyme disks and standard substrate disks were placed onto these plates with a plug of *P. ultimum* or *F. graminearum* culture. The reduction in colony growth was measured and compared to colony growth in the absence of biocidal enzymes and mancozeb.

Materials and Methods

Stabilized biocidal enzyme disk preparation. Dry enzyme disks were made by combining 3 μl KI (1 M), 5 μl NH4SCN (1 M), 175 μl 4% carboxymethyl cellulose (CMC), 295 μl stabilized lactoperoxidase+glucose oxidase (LPO+GOx) (119 nM+152.2 nM), and 3 μl blue food dye brought up to a final volume of 1 ml with DDI $H_2O$. Enzyme stabilization was performed as follows: lactoperoxidase (LPO) (125 μg/ml, pH 7.4) and glucose oxidase (GOx) (330 μg/ml, pH 7.4) were mixed to achieve a 1:1.3 M LPO:GOx ratio and stored on ice. Magnetite nanoparticles (NP) (1.277 mg/ml, pH 3, approximately 5 ml stock) were ultrasonicated at 40% amplitude for 1 min, cooled to ambient temperature (approximately 21° C.) in a water bath, and pipette mixed with the LPO:GOx enzyme suspension in a 1:1 enzyme:NP ratio. Dry substrate disks were made my combining 30 μl KI (1M), 50 μl $NH_4SCN$ (1M), 350 μl 4% CMC, 500 μl glucose (1M), and 3 μl red food dye brought up to a final volume of 1 ml with DDI $H_2O$. Dyes were included to differentiate enzyme disks from the substrate disks and were not biologically active or structural components of the disks. Each solution was pipette mixed several times and vortexed briefly. Solutions were dispensed in 50 μl aliquots onto parafilm and dried at ambient temperature in a vacuum oven containing desiccant at −50 kPa. After approximately 2 hours, dry enzyme and substrate disks were stored in the dark at 4° C. until use.

Mancozeb amended plates and culture growth assays. Corn meal agar (CMA) and potato dextrose agar (PDA) (for *P. ultimum* and *F. graminearum*, respectively) were amended with mancozeb flowable with zinc (Active ingredient (AI): mancozeb 37%, Bonide, Oriskany, N.Y.) to achieve final concentrations of 10 mg/l, 5 mg/l, 2 mg/l, 0.5 mg/l, and 0 mg/l (controls). Mancozeb and enzyme disk interactions were analyzed by placing one substrate disk on the center of each petri dish containing PDA amended with mancozeb (*F. graminearum*) or CMA amended with mancozeb (*P. ultimum*). These were followed by one enzyme disk and one culture plug mycelia-side down. Final enzyme concentrations in enzyme disks were 4 nM for *P. ultimum* and 119 nM for *F. graminearum* and based on results from preliminary enzyme formula optimization experiments. Plugs of *P. ultimum* measured 7 mm in diameter and plugs of *F. graminearum* measured 4 mm in diameter.

Preliminary testing revealed that *P. ultimum* is more sensitive to the enzyme treatment than *F. graminearum*. Thus, enzyme concentrations and plug sizes were chosen to achieve a measurable growth reduction, without being completely inhibitive, in enzyme-only treatments compared to non-treated controls. Each analysis included the same fungicide dilution series plated without substrate and enzyme disks as well as a substrate+enzyme disk-only treatment and a non-treated control. Each treatment was replicated once. Plates were left on the bench at ambient temperature for 2 days for *P. ultimum*, and 5 days for *F. graminearum*. Following the incubation period, control colonies had nearly grown to the plate edge. Two perpendicular colony diameter measurements were recorded for *P. ultimum*. Colonies of *F. graminearum* measured using the public domain image processing program ImageJ.

Results

Mancozeb combined with the stabilized enzyme formulation resulted in a statistically synergistic effect on *P. ultimum* at the lowest fungicide concentration and was additive at the three highest concentrations (Table 6). The combined effects were significantly greater than the effects of the enzyme formulation alone and all four fungicide concentrations alone. The effect of the enzyme formulation alone was significantly greater than the three lowest fungicide concentrations alone, but was not significantly different from the highest concentration alone (Table 6). Combined activity against *F. graminearum* was additive at all four fungicide concentrations (Table 6). The combined effects were significantly greater than the corresponding fungicide concentrations alone at the three highest concentrations. The effect of the enzyme formulation alone was not significantly different from any of the combined effects nor the fungicides alone (Table 6).

TABLE 6

Inhibition of *Pythium ultimum* and *Fusarium graminearum* by the stabilized LPO formulation alone and in combination with mancozeb using fungicide-amended media.

| Mancozeb concentration (mg/l) | Reduction in *P. ultimum* growth[a] | | | | Tukey's HSD | Combined effect (observed − expected)[b] | Combination result |
|---|---|---|---|---|---|---|---|
| | (+) enzyme | SD | (−) enzyme | SD | | | |
| 10 | 53% a[c] | 0.3% | 23% d | 1.7% | 6.04% | +4% | additive |
| 5 | 45% b | 0.5% | 16% e | 0.4% | | +3% | additive |
| 2 | 34% c | 1.3% | 10% e | 0.8% | | −2% | additive |
| 0.5 | 35% c | 3.7% | 2% f | 0.5% | | +7% | synergistic |
| 0 | 26% d | 0.9% | NA | NA | | | |

| Mancozeb concentration (mg/l) | Reduction in *F. graminearum* growth[a] | | | | Tukey's HSD | Combined effect (observed − expected)[b] | Combination result |
|---|---|---|---|---|---|---|---|
| | (+) enzyme | SD | (−) enzyme | SD | | | |
| 10 | 58% a[c] | 5.7% | 26% bcd | 6.0% | 32.4% | +3% | additive |
| 5 | 53% ab | 15.6% | 17% cd | 5.4% | | +7% | additive |
| 2 | 51% ab | 5.3% | 1% d | 5.1% | | +21% | additive |
| 0.5 | 39% abc | 10.9% | 6% cd | 3.8% | | +4% | additive |
| 0 | 29% abcd | 8.9% | NA | NA | | | |

[a]Reduction in growth relative to non-treated controls. Each value is the mean of two replicates.
[b]Difference between observed effect of fungicide (+) enzyme formulation and expected additive effect. Expected value calculated by adding the effect of fungicide alone and the effect of the enzyme formulation alone for each fungicide concentration.
[c]Means followed by the same letter are not significantly different, Tukey's HSD (P < 0.05).

All publications and patent documents disclosed or referred to herein are incorporated by reference in their entirety. The foregoing description has been presented only for purposes of illustration and description. This description is not intended to limit the invention to the precise form disclosed. It is intended that the scope of the invention be defined by the claims appended hereto.

What is claimed:

1. A seed, comprising a solid bactericidal coating, comprising;
   a) a first polymeric water-solvatable matrix material formulated with self-assembled mesoporous aggregates of magnetic nanoparticles comprising a hydrogen peroxide producing enzyme and a free radical producing enzyme;
   b) a second polymeric water-solvatable matrix material formulated with a first substrate for said hydrogen peroxide producing enzyme and a second substrate for said free radical producing enzyme; and
   c) a chemical antibiotic;
wherein said bactericidal coating is essentially inactive, wherein exposure of said first and second matrices to hydration or oxygen activates said coating and results in said substrate for said hydrogen peroxide producing enzyme being oxidized into hydrogen peroxide, wherein said hydrogen peroxide acts as a substrate for said free radical producing enzyme, and wherein said free radicals are produced having bactericidal activities, wherein said chemical antibiotic works synergistically with the bactericidal activity of said first and second matrices.

2. The seed of claim 1, wherein said chemical antibiotic is selected from the group consisting of ampicillin, streptomycin, vancomycin, and copper.

3. The seed of claim 1, wherein the solid bactericidal coating has a final chemical antibiotic concentration between about 1 and 100% of the minimum inhibitory concentration (MIC) or minimum bactericidal concentration (MBC).

4. The seed of claim 1, wherein said hydrogen peroxide producing enzyme is an oxidase.

5. The seed of claim 4, wherein said oxidase is glucose oxidase or alcohol oxidase.

6. An agricultural product, comprising the seed of claim 1.

7. The seed of claim 1, wherein said seed is selected from the group consisting of a vegetable seed, a fruit seed, a flower seed, and a field crop seed.

8. The seed of claim 7, wherein said vegetable seed is selected from the group consisting of tomato, pea, onion, garlic, parsley, oregano, basil, cilantro, carrot, cabbage, corn, cucumber, radish, pepper, broccoli, cauliflower, cucumber, spinach, kale, chard, artichoke, and lettuce.

9. The seed of claim 7, wherein said fruit seed is selected from the group consisting of citrus, tomato, orange, lemon, lime, avocado, clementine, apple, persimmon, pear, peach, nectarine, berry, strawberry, raspberry, grape, blueberry, blackberry, cherry, apricot, gourds, squash, zucchini, eggplant, pumpkin, coconut, guava, mango, papaya, melon, honeydew, cantaloupe, watermelon, banana, plantain, pineapple, quince, sorbus, loquata, plum, currant, pomegranate, fig, olive, fruit pit, a nut, peanut, almond, cashew, hazelnut, brazil nut, pistachio, and macadamia.

10. The seed of claim 7, wherein said field crop seed is selected from the group consisting of corn, wheat, soybean, canola, sorghum, potato, sweet potato, yam, lentils, beans, cassava, coffee, hay, buckwheat, oat, barley, rape, switchgrass, elephant grass, beet, sugarcane, and rice.

11. The seed of claim 7, wherein said flower seed is selected from the group consisting of annual, perennial, bulb, flowering woody stem, carnation, rose, tulip, poppy, snapdragon, lily, mum, iris, alstroemeria, pom, fuji, and bird of paradise.

12. A method of producing the seed of claim 1, said method comprising:
obtaining a seed,
formulating a solid bactericidal coating comprising
  a) a first polymeric water-solvatable matrix material formulated with self-assembled mesoporous aggregates of magnetic nanoparticles comprising a hydrogen peroxide producing enzyme and a free radical producing enzyme;
  b) a second polymeric water-solvatable matrix material formulated with a first substrate for said hydrogen peroxide producing enzyme and a second substrate for said free radical producing enzyme; and
  c) a chemical antibiotic;
  wherein said bactericidal coating is essentially inactive, wherein exposure of said first and second matrices to hydration or oxygen activates said coating and results in said substrate for said hydrogen peroxide producing enzyme being oxidized into hydrogen peroxide, wherein said hydrogen peroxide acts as a substrate for said free radical producing enzyme, and wherein said free radicals are produced having bactericidal activities, wherein said chemical antibiotic works synergistically with the bactericidal activity of said first and second matrices,
and coating the seed with the solid bactericidal coating.

13. The method of claim 12, wherein said first matrix material is further subjected to spray drying, freeze drying, drum drying, pulse combustion drying, or rotary seed coating.

14. The method of claim 12 wherein said second matrix material is further subjected to spray drying, freeze drying, drum drying, pulse combustion drying, or rotary seed coating.

15. A method of protecting a plant from a pathogen, comprising exposing the seed of claim 1 to hydration or oxygen prior to or during planting or germination of said seed.

16. The method of claim 15, wherein said pathogen is a bacterium selected from the group consisting of *Xanthomonas campestris, Clavibacter michiganensis, Acidovorax avenae, Pseudomonas viridiflava, Pseudomonas syringae, Escherichia coli, Salmonella* species, and *Listeria* species.

17. A method of reducing or eliminating damping off in a plant, comprising exposing the seed of claim 1 to hydration or oxygen.

\* \* \* \* \*